US009769455B2

(12) United States Patent
Fisker et al.

(10) Patent No.: US 9,769,455 B2
(45) Date of Patent: Sep. 19, 2017

(54) 3D FOCUS SCANNER WITH TWO CAMERAS

(75) Inventors: Rune Fisker, Virum (DK); Mike van der Poel, Rødovre (DK)

(73) Assignee: 3SHAPE A/S, Copenhagen K (DK)

( * ) Notice: Subject to any disclaimer, the term of this patent is extended or adjusted under 35 U.S.C. 154(b) by 893 days.

(21) Appl. No.: 13/996,739

(22) PCT Filed: Dec. 21, 2011

(86) PCT No.: PCT/DK2011/050507
§ 371 (c)(1),
(2), (4) Date: Oct. 8, 2013

(87) PCT Pub. No.: WO2012/083967
PCT Pub. Date: Jun. 28, 2012

(65) Prior Publication Data
US 2014/0022356 A1    Jan. 23, 2014

Related U.S. Application Data

(60) Provisional application No. 61/426,057, filed on Dec. 22, 2010.

(30) Foreign Application Priority Data

Dec. 21, 2010   (DK) .................................. 2010 01171

(51) Int. Cl.
*H04N 13/02*    (2006.01)
*A61B 5/00*    (2006.01)
(Continued)

(52) U.S. Cl.
CPC ....... *H04N 13/0203* (2013.01); *A61B 5/0062* (2013.01); *A61B 5/1076* (2013.01);
(Continued)

(58) Field of Classification Search
None
See application file for complete search history.

(56) References Cited

U.S. PATENT DOCUMENTS 6,839,513 B1 *   1/2005   Battles ..................... G03B 7/00
                                                      348/362
8,384,908 B2 *   2/2013   Sugita .................... A61B 3/102
                                                      356/479
(Continued)

FOREIGN PATENT DOCUMENTS

EP         1 941 843 A2     7/2008
EP         1941843 A2 *     7/2008 ............. A61B 5/107
WO     WO 2010/145669 A1   12/2010

OTHER PUBLICATIONS

International Search Report (PCT/ISA/210) issued on Mar. 6, 2012, by the Danish Patent Office as the International Searching Authority for International Application No. PCT/DK2011/050507.
(Continued)

*Primary Examiner* — Joseph Ustaris
*Assistant Examiner* — Edemio Navas, Jr.
(74) *Attorney, Agent, or Firm* — Buchanan Ingersoll & Rooney PC

(57) ABSTRACT

A scanner for obtaining and/or measuring a 3D geometry of a surface of an object includes a camera having an array of sensor elements, a first device for generating a probe light, a device for transmitting the probe light rays towards the object, a device for transmitting light rays returned from the object to the array of sensor elements, an optical system for imaging with a first depth of field on the camera the transmitted light rays, a device for varying the position of the focus plane on the object, a device for obtaining at least one image from said array of sensor elements, a device for
(Continued)

determining the in-focus position(s) of sensor elements, and a device for transforming the in-focus data into 3D coordinates.

22 Claims, 15 Drawing Sheets

(51) Int. Cl.
    *A61B 5/107* (2006.01)
    *A61C 9/00* (2006.01)
    *G01B 11/24* (2006.01)
    *G01B 11/25* (2006.01)

(52) U.S. Cl.
    CPC ............ *A61B 5/1079* (2013.01); *A61B 5/441* (2013.01); *A61B 5/4542* (2013.01); *A61C 9/0066* (2013.01); *G01B 11/24* (2013.01); *G01B 11/2513* (2013.01)

(56) References Cited

U.S. PATENT DOCUMENTS

| | | | |
|---|---|---|---|
| 2005/0083536 A1* | 4/2005 | Fouquet | A61B 5/0066 |
| | | | 356/512 |
| 2006/0001739 A1 | 1/2006 | Babayoff | |
| 2006/0139475 A1* | 6/2006 | Esch | G03B 37/04 |
| | | | 348/340 |
| 2007/0029233 A1* | 2/2007 | Reinhold | B07C 5/3416 |
| | | | 209/578 |
| 2009/0079861 A1 | 3/2009 | Liao | |
| 2009/0182690 A1* | 7/2009 | Stein | G01J 1/04 |
| | | | 706/12 |
| 2009/0279103 A1 | 11/2009 | Thiel et al. | |
| 2011/0128385 A1* | 6/2011 | Bedros | H04N 5/232 |
| | | | 348/164 |

OTHER PUBLICATIONS

Danish Search Report issued on Jul. 15, 2011.
Danish Office Action issued on Jul. 9, 2011.

* cited by examiner

3D FOCUS SCANNER WITH TWO CAMERAS

This invention generally relates to a 3D focus scanner. More particularly, the invention relates to an optical system in a 3D focus scanner.

Disclosed is a scanner for obtaining and/or measuring a 3D geometry of at least a part of a surface of an object, said scanner comprising:
- a first camera comprising an array of sensor elements,
- a first means for generating a probe light,
- means for transmitting the probe light rays towards the object thereby illuminating at least a part of the object,
- means for transmitting light rays returned from the object to the array of sensor elements,
- a first optical system for imaging with a first depth of field on the first camera at least part of the transmitted light rays returned from the object to the array of sensor elements,
- means for varying the position of the focus plane on the object,
- means for obtaining at least one image from said array of sensor elements,
- means for determining the in-focus position(s) of:
  - each of a plurality of the sensor elements for a range of focus plane positions, or
  - each of a plurality of groups of the sensor elements for a range of focus plane positions, and
- means for transforming the in-focus data into 3D coordinates.

According to an aspect of the focus scanning apparatus, is disclosed a scanner for obtaining and/or measuring a 3D geometry of at least a part of a surface of an object, said scanner comprising:
- a first camera comprising an array of sensor elements,
- a first means for generating a probe light,
- means for transmitting the probe light rays towards the object thereby illuminating at least a part of the object,
- means for transmitting light rays returned from the object to the array of sensor elements,
- a first optical system for imaging with a first depth of field on the first camera at least part of the transmitted light rays returned from the object to the array of sensor elements,
- means for varying the position of the focus plane on the object,
- means for obtaining at least one image from said array of sensor elements,
- means for determining the in-focus position(s) of:
  - each of a plurality of the sensor elements for a range of focus plane positions, or
  - each of a plurality of groups of the sensor elements for a range of focus plane positions, and
- means for transforming the in-focus data into 3D coordinates;
- means for selecting a portion of light rays returned from the object, where the light rays have been transmitted through at least a part of the first optical system; and
- a second camera for capturing at least some of the selected light rays with a second depth of field which is substantially larger than the first depth of field.

In some embodiments, the second camera is configured for obtaining images with a second depth of field. In some embodiments, the scanner comprises optical components arranged to image at least part of the selected portion of the light rays returned from the object onto the second camera with a second depth of field.

In some embodiments, the in-focus position of a sensor element corresponds to the position of the focus plane in which the focus plane intersects a portion of the object surface and where the light rays returning from this portion of the object surface are imaged onto this particular sensor element. In embodiments, where a pattern is arranged to provide structure to the probe light, the in-focus position for a given sensor element may correspond to the position of the focus plane where the pattern is in focus on the object being scanned for this sensor element. The first camera may record a high value of the correlation measure for that sensor element at the in-focus position, when the position of the focus plane is varied over a range of values.

In some embodiments, the first depth of field is in the range of about 5 µm to about 1000 µm, such as in the range of about 10 µm to about 500 µm, such as in the range of about 50 µm to about 250 µm, such as in the range of about 75 µm to about 150 µm, In some embodiments, the second depth of field is in the range of about 1 mm to about 150 mm, such as in the range of about 3 mm to about 100 mm, such as in the range of about 5 mm to about 50 mm, such as in the range of about 10 mm to about 30 mm, such as in the range of about 15 mm to about 25 mm.

In some embodiments, the depth of the scan volume of the scanner as measured from the scanner is in the range of about 3 mm to about 100 mm, such as in the range of about 5 mm to about 50 mm, such as in the range of about 10 mm to about 30 mm, such as in the range of about 15 mm to about 25 mm, In some embodiments, the ratio between the second depth of field and the depth of the scan volume of the scanner is in the range of about 0.1 to about 10, such as in the range of about 0.2 to about 5, such as in the range of about 0.25 to about 4, such as in the range of about 0.4 to about 2.5, such as in the range of about 0.5 to about 2, such as in the range of about 0.7 to about 1.5, such as in the range of about 0.8 to about 1.25, such as in the range of about 0.9 to about 1.1.

In some embodiments, the ratio between the second depth of field and the first depth of field is in the range of about 10 to about 2000, such as in the range of about 25 to about 1000, such as in the range of about 50 to about 750, such as in the range of about 75 to about 500, such as in the range of about 100 to about 400, such as in the range of about 125 to about 300, such as in the range of about 150 to about 200.

In some embodiments, the means for transmitting light rays returned from the object to the array of sensor elements are the same as the means for transmitting the probe light rays towards the object. That is, the light rays returned from the object to the array of sensor elements are transmitted by the optical components that also are used for transmitting the probe light rays towards the object.

One advantage of a configuration where the light rays are transmitted to and from the object by the same optical components is that the number of optical components the system can be kept at a minimum, such that a more compact scanner can be realized.

In some embodiments, the means for transmitting the probe light rays towards the object and the means for transmitting the light rays returned from the object to the array of sensor elements are at least partly separate such that at least one or both of these means comprises an optical component it does not share with the other.

In some embodiments, the means for transmitting the probe light rays towards the object and the means for transmitting the light rays returned from the object to the array of sensor elements are separated such that each of these means are made from optical components it does not share with the other.

One advantage of a configuration where at least some of the optical components used for transmitting the light rays to and from the object are different is that the light rays returning from the object can be manipulated in a different manner than light rays were manipulated on their way from the light source to the object. One filter may for instance be added in the means for transmitting the light rays returned from the object to the array of sensor elements and another filter in the means for transmitting the probe light rays towards the object.

In some embodiments, at a part of the means for transmitting the probe light rays towards the object and/or at a part of the means for transmitting light rays returned from the object to the array of sensor elements are at least partly separate from the first optical system.

In some embodiments, the means for transmitting the probe light rays towards the object and/or the means for transmitting light rays returned from the object to the array of sensor elements are integrated parts of the first optical system.

In some embodiments, the means for transmitting the probe light rays towards the object comprises an arrangement of optical components, such as lenses and mirrors, arranged for transmitting the probe light from the first light source towards the object.

In some embodiments, the means for transmitting light rays returned from the object to the array of sensor elements may comprise an arrangement of optical components, such as lenses and mirrors, arranged for transmitting the light rays returned from the object to the array of sensor elements.

In some embodiments, the first optical system comprises an arrangement of lenses for transmitting the probe light towards the object and for imaging with a first depth of field at least part of the transmitted light rays returned from the object onto the array of sensor elements. The probe light may be transmitted onto the object along the same optical axis of the first optical system as the light rays returned from the object are transmitted along.

In the context of the present invention, the phrase "scanner" and "focus scanning apparatus" may be used interchangeably.

In some embodiments, the first camera consists of a charge-coupled device (CCD). In this case, the light rays may travel directly from the first optical system to the CCD without passing any further beam shaping optics.

In some embodiments, the first camera consists of a charge-coupled device (CCD) and at least one beam shaping optical component such as a filter or a lens.

The invention generally relates to three dimensional (3D) scanning of the surface geometry of objects. A focus scanning apparatus perform a non-contact 3D scanning of an object by obtaining a series of images for different focus planes on the object and determining in-focus regions for the obtained images. This is done by means of a camera comprising an array of sensor elements and imaging optics where the focus plane on the object can be varied. The in-focus data is transformed into 3D real world coordinates thereby obtaining a 3D surface or 3D model of the object. For the purpose of 3D scanning it is advantageous to obtain images with a shallow depth of field so that in-focus positions are determined with high accuracy.

In some embodiments, the focus scanning apparatus comprises a second camera used for obtaining an image with a large depth of field while obtaining shallow depth of field images needed for the 3D scanning with the first camera in the apparatus. The large depth of field image may have such a large depth of field that all scanned parts of the object are in focus. The large depth of field image may also have the same perspective as the shallow depth of field images.

It is an advantage of obtaining such a large depth of field image that the large depth of field image may be used as assistance when the scanner operator aims the scanner onto the object being scanned. In this case the large depth of field image may be displayed on some display.

It is a further advantage that if the large depth of field image has a fixed perspective with respect to the shallow depth of field images, then there exists a correspondence between the 3D scanned surface and the large depth of field image. This may be used to overlay texture obtained in the large depth of field image onto the 3D scanned surface constructed from in-focus data in the series of images obtained by means of the first camera.

Furthermore, it is an advantage that the large depth of field image can have a larger field of view than the shallow depth of field images. This may assist in aiming the scanner properly for 3D scanning of a certain region.

Furthermore, it is an advantage that the large depth of field image can have a large frame rate, such as e.g. 30 fps or 60 fps. In a hand-held focus scanner the high frame rate may be used for tracking the relative motion of the scanner and the object being scanned by analyzing the motion of feature points in the large depth of field images.

Furthermore, it is an advantage that the large depth of field image can be in colors. This may allow for overlay of color texture onto the 3D scanned surface, such as by a registration of the color texture onto the 3D scanned surface. A relation between the pixels of the images obtained by the first and the second camera can provided by e.g. a calibration scanning of a calibration object or be precise alignment of the different parts of the scanner.

Furthermore, it is an advantage that a large depth of field image in color can be used for distinguishing different materials or surfaces on the object being scanned. Such a distinction can be useful in further treatment of the 3D data of the object.

Furthermore, for the purpose of 3D scanning it may be advantageous to use polarization optics to enhance specular reflections from the surface of the object being scanned. Such specular reflections, however, can contain highlights. The large depth of field image can be captured with polarizing optics to reduce specular reflections. For color measurements this may be particularly advantageous. Thus it becomes possible to obtain information of the scanned object from light returned from the object where both specular reflections have been enhanced—for the 3D scanning—and where specular reflections have been inhibited—for the large depth of field image. Such polarization information can be advantageous to use in e.g. color analysis of the object being scanned.

Furthermore, it is an advantage that the information in the large depth of field image can be used to distinguish different types of material and/or surfaces on the object being scanned. This is in particular true if the large depth of field image contains color information.

Furthermore, it is an advantage that it is possible to perform a spectral analysis of the large depth of field image obtained by means of the second camera: This may be done by selecting a 1D portion of the light rays returned from the object, such that the large depth of field image is 1D. In this case it becomes possible to use one axis of the 2D second camera as a spatial axis and the other axis as a spectral axis.

Such spectral analysis can be useful for detailed color measurement or determination of material composition in the surface.

In the context of the present invention, the phrase "1D portion" may refer to a portion with a width which is substantially smaller than its dimension along its longitudinal axis, such as about 100 times smaller, such as about 50 times smaller such as about 25 times smaller such as about 10 times smaller such as about 5 times smaller. In some embodiments the width of the 1D portion is smaller than about 5 mm, such as smaller than about 2.5 mm, such as smaller than about 1 mm, such as smaller than about 0.5 mm, such as smaller than about 0.25 mm, such as smaller than about 0.1 mm.

The apparatus is particularly suited for intraoral scanning, i.e. direct scanning of teeth and surrounding soft-tissue in the oral cavity. Other dental related applications of the invention are for scanning dental impressions, gypsum models, wax bites, dental prosthetics and abutments.

The apparatus is also suited for scanning of the interior and exterior part of a human ear or of ear channel impressions.

The apparatus may also be used within scanning of the 3D structure of skin in dermatological or cosmetic/cosmetological applications, scanning of jewelry or wax models of whole jewelry or part of jewelry, scanning of industrial parts and even time resolved 3D scanning, such as time resolved 3D scanning of moving industrial parts.

Creating a Large Depth of Field (DOF) Image

In some embodiments the second camera is adapted for forming at least one image in 1D and/or 2D of at least some of the selected light rays.

In some embodiments the second depth of field image has a fixed perspective relative to the perspective of the first depth of field image(s).

In some embodiments the second depth of field image has substantially the same perspective as the first depth of field image(s).

In some embodiments the second depth of field image is substantially unaffected by varying the position of the focus plane on the object.

In some embodiments the means for selecting a portion of light rays returned from the object is arranged in an aperture in the first optical system.

In some embodiments the means for selecting a portion of light rays is arranged between the first optical system and focusing optics of the scanner.

In some embodiments the means for selecting a portion of light rays is arranged between the focusing optics of the scanner and the part of the scanner where light rays exit and/or enter the scanner.

In some embodiments the means for selecting a portion of light rays is a second optical element arranged in the aperture to select light rays from a region of the aperture for obtaining the second depth of field image(s).

In some embodiments the region of the aperture, where light rays is selected from, is small relative to the total area of the aperture, such as less than 50% of the area of the aperture, such as less than about 40% of the area of the aperture, such as less than about 30% of the area of the aperture, such as less than about 20% of the area of the aperture, such as less than about 10% of the area of the aperture, such as less than about 5% of the area of the aperture, such as less than about 2% of the area of the aperture, such as less than about 1% of the area of the aperture.

In some embodiments the selected light rays are deflected in a different direction than the direction of the first optical system.

In some embodiments the deflected rays are directed to a second optical system for imaging onto the second camera.

In some embodiments the first camera and the second camera are adapted to operate simultaneously.

In some embodiments the second optical element in the aperture is a mirror.

In some embodiments the second optical element in the aperture is a beam splitter.

In some embodiments the second optical element in the aperture is a filter adapted to select light rays of one or more specific wavelengths.

In some embodiments the second optical element in the aperture is small relative to the total area of the aperture, such as less than 50% of the area of the aperture, such as less than about 40% of the area of the aperture, such as less than about 30% of the area of the aperture, such as less than about 20% of the area of the aperture, such as less than about 10% of the area of the aperture, such as less than about 5% of the area of the aperture, such as less than about 2% of the area of the aperture, such as less than about 1% of the area of the aperture.

The size of the second optical element may be e.g. between 1% and 10% of the size of the aperture. The diameter of the second optical element may be e.g. 2-3 mm. Due to the small size of the second optical element, the second optical element will most likely not affect the focus scanning.

The image which is acquired with the second camera may correspond to what is captured with the first camera, i.e. the view, the perspective etc. may the same for images acquired with both cameras. Because the optical elements functions as a very small aperture, the depth of field of the second camera becomes very large, and thus everything in the images captured with the second camera may be in focus at the same time. The image acquired with the second camera may work as an assisting image for the operator of the scanner. Thus the depth of field is very small or shallow in the images obtained by the first camera for the focus scanning, and the depth of field is very large for the assisting image obtained by the second camera.

In some embodiments, the scanner comprises an aperture with an effective area over which effective area light rays retuning from the object are allowed to pass through the aperture towards the first camera.

In some embodiments, the aperture is defined by a first optical element of the scanner, where the first optical element is capable controlling the effective area of the aperture.

In some embodiments, the scanner comprises a first optical element arranged in said aperture in such a manner that the first optical element is capable controlling the effective area of the aperture.

The first optical element may operate in combination with a separate aperture of the scanner or it may operate alone to define the aperture.

The first optical element may be capable of controlling the effective area of the aperture, such that the effective area can be changed between a relatively larger effective aperture area and a relatively smaller effective aperture area.

With the first optical element in a configuration corresponding to the relatively larger effective aperture area, at least part of the transmitted light rays returned from the object is imaged on the first camera with a first depth of field. With the first optical element in the configuration corresponding to the relatively smaller effective aperture area, at least part of the transmitted light rays returned from the object is imaged on the first camera with a second depth of field, where the second depth of field is larger than the first depth of field. I.e., switching between these two configurations of the first optical element provides that the first optical system can image onto the first camera the transmitted light rays returned from the object both with the first depth of field and with the second depth of field.

Embodiments of the scanner providing control over the size of the aperture can thus have the advantage that a single camera can be used for obtaining both the shallow depth of field images and the large depth of field images.

In some embodiments, the first optical element is configured for switching the effective area of the aperture between the relatively larger effective area and the relatively smaller effective area in such a manner that the ratio between the relatively larger effective area and the relatively smaller effective area may be in the range of about 1.2 to about 100, such as in range of about 1.4 to about 50, such as in range of about 1.7 to about 35, such as in range of about 2 to about 25, such as in range of about 2.5 to about 16, such as in range of about 2 to about 10, such as in range of about 3 to about 8.

In some embodiments the first optical element is configured to switch between selecting substantially all light rays impinging on the aperture and only selecting a portion of the light rays impinging the aperture.

The configuration of the first optical element corresponding to the relatively larger effective aperture area may be such that substantially all light rays impinging on the aperture are allowed to pass through the aperture to the first camera.

The configuration of the first optical element corresponding to the relatively smaller effective aperture area may be such that only the selected portion of the light rays impinging the aperture are allowed to pass through the aperture to the first camera.

In some embodiments the selected portion of light rays impinging on the aperture is small relative to all the light rays impinging the aperture, such as less than 50% of all light rays, such as less than about 40% of all light rays, such as less than about 30% of all light rays, such as less than about 20% of all light rays, such as less than about 10% of all light rays, such as less than about 5% of all light rays, such as less than about 2% of all light rays, such as less than about 1% of all light rays.

In the context of the present invention, an optical element may be said to be arranged in the aperture when it is arranged in such a manner that at least part of the element is within a volume extending along the optical axis with a cross section defined by the aperture, i.e. by the opening of the aperture. At least said part of the optical element is hence visible from both sides of the aperture when viewing the opening of the aperture along the optical axis.

When an optical element is arranged in the aperture at least a portion of the light rays returning from the object and propagating along the optical axis may impinge on the optical element.

In some cases an optical element can be said to be arranged in the aperture if it will collide with the aperture when moved perpendicular to the optical axis. The extension of said volume from the aperture may then be substantially zero.

In some cases an optical element can be said to be arranged in the aperture if said volume extends a distance from the aperture, such as a distance of less than about 10 mm from the aperture, such as less than about 8 mm from the aperture, such as less than about 5 mm from the aperture, such as less than about 3 mm from the aperture, such as less than about 2 mm from the aperture, such as less than about 1 mm from the aperture. The optical element may then be said to be arranged in the aperture even if it would stay clear of the aperture if moved perpendicular to the optical axis.

In some embodiments the first optical element configured to switch comprises a liquid crystal.

In some embodiments the first optical element and/or the second optical element is configured for controlling the polarization of the light rays.

Besides the different optical elements already mentioned, the first and/or second optical elements may be polarizers, lenses, gratings, retardation plates, glass with coatings, such as evaporated coatings or spotted coatings.

In some embodiments means for polarizing the light rays is arranged in front of the first means for generating a probe light and/or in front of the second camera. Thus polarization control can be provided. In some cases, it is an advantage to provide crossed polarizers in front of light source and second camera.

Color Images and Second Light Sources

In some embodiments the probe light is substantially white light and the first means for generating a probe light is a first light source configured for emitting white light, such as a white phosphorous InGaN LED or a supercontinuum light source.

In some embodiments the scanner comprises a second means for generating a probe light which is not used for determining the in-focus positions.

In some embodiments the second means for generating a probe light generates white light. The second means for generating a probe light may be a second light source configured for emitting white light, such as a white phosphorous InGaN LED or a supercontinuum light source In some embodiments the second camera is a color camera.

In some embodiments the color camera comprises a 2D array of photo sensors and a color filter array.

In some embodiments the color filter array is a Bayer filter array.

In some embodiments the color filter array comprises more than three filters.

In some embodiments the color camera comprises a trichroic beam splitter and three different sensors to obtain images of the individual colors.

In some embodiments, the color of the probe light generated by the second means is adapted to be changed.

In some embodiments, the second means is capable of changing the color of the probe light it generates.

In some embodiments the second means for generating probe light is LEDs of different colors.

In some embodiments the differently colored LEDs are adapted to be activated at different times, and whereby black and white images are adapted to be recorded with the second camera, and where the black and images are adapted to be combined to a full-color image.

The second camera can be arranged as close as possible to the aperture for reducing the distance the light rays must travel for hitting the sensors in the camera. However, the second camera can also be arranged in the end of the scanner pointing away from the object to be scanned, since this may allow for a more slender scanner.

Line Spectral Measurement

According to an aspect of the focus scanning apparatus, disclosed is a scanner for obtaining and/or measuring a 3D geometry of at least a part of a surface of an object, said scanner comprising:
- a first camera comprising an array of sensor elements,
- a first means for generating a probe light,
- means for transmitting the probe light rays towards the object thereby illuminating at least a part of the object,
- means for transmitting light rays returned from the object to the array of sensor elements,
- a first optical system for imaging with a first depth of field on the first camera at least part of the transmitted light rays returned from the object to the array of sensor elements,
- means for varying the position of the focus plane on the object,
- means for obtaining at least one image from said array of sensor elements,
- means for determining the in-focus position(s) of:
  - each of a plurality of the sensor elements for a range of focus plane positions, or
  - each of a plurality of groups of the sensor elements for a range of focus plane positions, and
- means for transforming the in-focus data into 3D coordinates;

wherein the scanner further comprises means for performing spectral analysis of the light returned from the object.

In some embodiments the means for performing spectral analysis is in a 1D array.

In some embodiments points or sections in the 1D image are spectrally analyzed.

In some embodiments the 1D spectral analysis is performed on the second camera comprising a 2D array, where one axis of the camera array corresponds to a spatial coordinate on the object being scanned and the other axis of the camera array corresponds to a wavelength coordinate of the light returned from the object.

In some embodiments, one dimension of the second camera is used as a spatial dimension while the other dimension of the second camera is used as a spectral dimension.

This may achieved in the following way: a portion of the light rays returning from the object is selected by the second optical element and imaged onto a slit which selects a 1D portion of the 2D distribution of the light rays. The 1D portion is then projected onto a diffractive optical component, such as a grating, where the diffractive optical component is arranged to diffract each section of the 1D portion into a plane perpendicular to the long axis of the 1D portion. Additional optics may be arranged to guide the diffracted light rays onto the 2D array of sensor elements in the second camera such that different wavelengths of the light in one section is diffracted into a wavelength specific angle and hence onto a wavelength specific sensor element. There is hence a correlation between each sensor element in the array of sensor elements and the wavelength of light rays in a section of the selected 1D portion. From knowledge of this correlation, obtained e.g. by a previous calibration of the scanner, a spectrum can be obtained for each section of the 1D portion. In this case the second light source may be a white-light source, and it is understood that the second light source can comprise collimation optics.

In some embodiments the spectrally analyzed light is a portion of light rays returned from the object and transmitted through at least a part of the first optical system. The scanner may comprise an element configured for selecting a portion of light rays returned from the object, such as a slit.

In some embodiments the spectral analysis is performed by means of a diffractive optical component.

In some embodiments the diffractive optical component is a grating.

In some embodiments the spectral analysis is performed by means of a prism.

In some embodiments the spectral analysis is performed by means of a color gradient film.

Combination of 3D Focus Scanner with a Color Measurement Probe

A prior art color measuring probe is the probe disclosed in U.S. Pat. No. 5,745,299, which is a probe comprising a central light source and a number of receivers. The probe must be moved towards/away from the object to be color measured, e.g. a tooth, during the color measurement, because the probe cannot measure the 3D geometry of the object, and therefore redundancy is necessary for validating the color measurement.

However, in the present focus scanning apparatus, the color measurement can be obtained without having to move the color measuring probe towards/away from the object, because the 3D geometry of the object is known, the distance etc. between the light source(s) and the light sensor(s) is known, the surface which is color measured is known and the inclination/curvature of the surface is known.

Since the geometry is known, a geometrically conditional correction of the measured values can be performed and the color can be derived independently of the geometry.

In some embodiments, a color measuring probe is attached to the focus scanning apparatus in such a way that the color measuring probe can obtain data from one section of a scanned object while another section of the object can be 3D scanned by the focus scanning optics of the scanner. The color measuring probe may be configured for measuring the color of a surface it is brought into contact with and the color measuring probe may be attached to the focus scanning apparatus in such a manner that it can be brought into contact with an object while the focus scanning apparatus is still capable of scanning the object.

From knowledge of the optics of the focus scanning apparatus and the fixed relative position of the color measuring probe and the focus scanning apparatus a correlation between the color data obtained by the color measuring probe and the 3D coordinates obtained simultaneously by the focus scanning apparatus can be obtained. A registration of the color data into a 3D model of the object formed by e.g. triangulation of the obtained 3D coordinates can be provided based on this correlation.

The focus scanning apparatus and the color measuring probe may be calibrated, such that the color measurement can be correctly combined with/related to the 3D geometry of the object.

The color measuring probe may be a fiber probe, which is flexible and bendable.

The color measuring probe may perform a color measurement which allows for distinguishing between the teeth and the tissue in the mouth.

The color measuring probe may measure the color of different regions on a tooth, such that the original colors of the tooth can be reproduced in a restoration.

The color measurement may be used to determine the exact margin line on teeth.

The color measurement may comprise measuring texture of the surface of the object.

By means of a regular 2D color image of the patient's teeth and a color measurement of e.g. points on the patient's teeth, by means of the color measuring probe, a relative color determination of the teeth can be performed.

According to an aspect of the focus scanning apparatus, disclosed is a scanner for obtaining and/or measuring a 3D geometry of at least a part of a surface of an object, said scanner comprising:
- a first camera comprising an array of sensor elements,
- a first means for generating a probe light,
- means for transmitting the probe light rays towards the object thereby illuminating at least a part of the object,
- means for transmitting light rays returned from the object to the array of sensor elements,
- a first optical system for imaging with a first depth of field on the first camera at least part of the transmitted light rays returned from the object to the array of sensor elements,
- means for varying the position of the focus plane on the object,
- means for obtaining at least one image from said array of sensor elements,
- means for determining the in-focus position(s) of:
  - each of a plurality of the sensor elements for a range of focus plane positions, or
  - each of a plurality of groups of the sensor elements for a range of focus plane positions, and
- means for transforming the in-focus data into 3D coordinates;

wherein the scanner further comprises a color measuring probe rigidly attached to the 3D scanner.

The color measuring probe may be suitable for measuring colors and/or translucency of e.g. teeth.

The color measuring probe may be incorporated in the focus scanning apparatus, or be removably attached to the scanner, such as by snapping etc.

In some embodiments the color measuring probe is a probe suitable for measuring tooth shades.

In some embodiments the color measuring probe is configured to perform the measurement in at least one point on a tooth.

In some embodiments the position of the point measurement and/or the orientation of the color measurement probe relative to the object is derivable due to the rigid attachment of the color measuring probe relative to the scanner.

In some embodiments the color measuring probe is adapted to be arranged perpendicular to a surface of the object.

In some embodiments the color measuring probe is a spectrophotometer system comprising:
- a probe tip including one or more light sources and a plurality of light receivers;
- a first spectrometer system receiving light from a first set of the plurality of light receivers;
- a second spectrometer system receiving light from a second set of the plurality of light receivers;
- a processor, wherein the processor receives data generated by the first spectrometer system and the second spectrometer system, wherein an optical measurement of the object is produced based on the data generated by the first and second spectrometer systems.

In some embodiments the color measuring probe is for determining optical characteristics of a translucent dental tooth, comprising:
- a probe with a tip adapted to provide light to a surface of the tooth from at least one light source, and to receive light from the tooth through at least one light receiver, the at least one light source and the at least one light receiver being spaced apart to define a minimal height as a predetermined distance from the surface below which no light from the at least one light source that is specularly reflected from said surface is received by the at least one light receiver,
- light sensors coupled to the at least one light receiver for determining the intensity of light received by the light receiver, when the probe is at a point away from the surface of the tooth but less than the minimal height; and
- a computing device coupled to the light sensors.

Angled Mirrors and Scanning with Dual/Multiple Views Simultaneously

When scanning objects it is often necessary to obtain scans from different perspectives to obtain a sufficient model of the object being scanned. An example could be the scanning of a tooth prepared for a dental restoration such as a crown and the neighboring teeth. In such a scanning situation it is necessary to scan the proximal surfaces of neighboring teeth to identify e.g. contact points on the proximal surfaces. If the scanner provides a scan with one perspective for a given relative position of the scanner and the teeth being scanned it is necessary to move the scanner to different positions and obtain individual scans in these positions. A sufficient 3D model of the scanned teeth may then be obtained by e.g. stitching of the individual scans. Such a movement of the scanner may be difficult to perform inside the oral cavity due to space limitations. It is an advantage to design the optical system in the scanner so that it may obtain more than one view even if held in one relative position relative to the teeth being scanned. Ideally, a scanner with more than one view can make a sufficient scan from just a single relative position of the scanner and the teeth being scanned. But even if a scanner that can obtain scans with more than one perspective cannot obtain a sufficient scan from a single relative position to the teeth it may still be an advantage. It may be possible that the relative movement needed is smaller than if the scanner did not have the ability to obtain scans with more than one perspective. It may also be an advantage that the scanner with more than one view is faster to operate.

US2009/0279103 discloses an apparatus for optical 3D measurement, comprising a first beam deflector for deflecting an illuminating beam onto an object to be measured and for deflecting the monitoring beam reflected from the object to be measured, wherein said first beam deflector can be moved along a path distance S. The movable deflector or translation of the deflector is provided for the purpose of reducing the height of the scanning tip in the apparatus. The present scanner eliminates the need for a movable beam deflector.

According to an aspect of the focus scanning apparatus, disclosed is a scanner for obtaining and/or measuring a 3D geometry of at least a part of a surface of an object, said scanner comprising:
- a first camera comprising an array of sensor elements,
- a first means for generating a probe light,
- means for transmitting the probe light rays towards the object thereby illuminating at least a part of the object,
- means for transmitting light rays returned from the object to the array of sensor elements,
- a first optical system for imaging with a first depth of field on the first camera at least part of the transmitted light rays returned from the object to the array of sensor elements, means for varying the position of the focus plane on the object, means for obtaining at least one image from said array of sensor elements, means for determining the in-focus position(s) of:
  each of a plurality of the sensor elements for a range of focus plane positions, or
  each of a plurality of groups of the sensor elements for a range of focus plane positions, and means for transforming the in-focus data into 3D coordinates;

wherein the scanner further comprises at least one reflective optical element arranged in the scanner such that the reflective optical element provides for that at least two different perspective views on the acquired images is obtainable without performing movement of the scanner.

In some embodiments the scanner further comprises means for obtaining a first set of 3D scans and a second set of 3D scans, where the perspective views are different in the first set and in the second set of scans.

In some embodiments a first set of images with a first perspective view and a second set of images with a second perspective view are acquired simultaneously or concurrently.

In some embodiments, the scanner comprises means for obtaining 3D scans with more than one perspective. A 3D scan is made from 2D images acquired with the focus optics.

In some embodiments the first perspective view is fixed relative to the second perspective view.

Thus the perspectives are fixed relative to each other.

In some embodiments the scanner comprises means for switching between different perspective views of the images acquired using the first camera.

In this case it is possible to switch between different perspectives of the images on the first camera. Thus there is more than one perspective in the image, but only one perspective is shown at the time.

In some embodiments the scanner comprises means for combining images with different perspective views acquired using the first camera.

In this case the scanner comprises means for combining images of more than one perspective onto the first camera, thus enabling simultaneous scanning with more than one perspective.

In some embodiments the at least one reflective optical element is arranged in the tip of the scanner which is configured for pointing towards the object to be scanned.

In some embodiments the at least one reflective optical element comprises two dichroic mirrors or filters.

One of the mirrors or filters may be transparent to e.g. red light, and the other mirror or filter may be transparent to e.g. blue light. If the mirrors or filter are arranged in favorable positions, the scanner can scan in different directions simultaneously or concurrently, and hereby for example two different surfaces of a tooth may be scanned at one go, e.g. the lingual surface and the labial surface.

In some embodiments the at least one reflective optical element comprises a multi-facet mirror.

In some embodiments the at least one reflective optical element comprises a digital light processing (DLP).

The at least one reflective optical element may comprise pericentrical optics.

In some embodiments the at least one reflective optical element and/or the other optical elements is/are adapted to generate one or more patterns to be imaged on the object while scanning.

In some embodiments the tip of the scanner is exchangeable, and where at least two different tips are adapted to fit on the scanner, where one of the tips comprises one or more mirrors arranged at about 38 degrees relative to an axis perpendicular to the optical axis, and where another of the tips comprises one or more mirrors arranged at about 45 degrees relative to an axis perpendicular to the optical axis.

The different tips may be in different colors for easy recognition by the dentist.

In some embodiments, such a tip comprises one or more mirrors arranged at an angle in the range of about 25 degrees to about 50 degrees relative to an axis perpendicular to the optical axis, and another of the tips comprises one or more mirrors arranged at an angle in the range of about 30 degrees to about 60 degrees relative to an axis perpendicular to the optical axis.

In some embodiments the 3D scanning is an intra oral scanning of at least part of a patient's set of teeth, a scan of at least part of an impression of a patient's set of teeth, and/or a scan of at least part of a model of a patient's set of teeth.

US2009/0279103 discloses an apparatus for optical 3D measurement, comprising a first beam deflector for deflecting an illuminating beam onto an object to be measured and for deflecting the monitoring beam reflected from the object to be measured, wherein said first beam deflector can be moved along a path distance S. The movable deflector or translation of the deflector is provided for the purpose of reducing the height of the scanning tip in the apparatus.

U.S. Pat. No. 7,319,529 describes a retracting aperture stop that allows to stop down system aperture in preview mode before scanning. Our invention eliminates the need for a retracting aperture stop and allows viewing the scanned object with a large depth of field at the same time as scanning is performed.

U.S. Pat. No. 7,319,529 describes how a second light source illuminating the object with a low numerical aperture can be used to generate a preview image of the object. Our invention may be used without the need for a second light source or with a second light source with a high numerical aperture.

The present invention relates to different aspects including the apparatuses described above and in the following, and corresponding methods, devices, apparatuses, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a method for obtaining and/or measuring a 3D geometry of at least a part of a surface of an object, said method comprising:
  generating a probe light by means of a first means for generating probe light,
  transmitting the probe light rays towards the object thereby illuminating at least a part of the object,
  transmitting light rays returned from the object to an array of sensor elements in a first camera,
  imaging with a first depth of field on the first camera at least part of the transmitted light rays returned from the object to the array of sensor elements by means of a first optical system,
  varying the position of the focus plane on the object,
  obtaining at least one image from said array of sensor elements, determining the in-focus position(s) of:
 each of a plurality of the sensor elements for a range of focus plane positions, or
 each of a plurality of groups of the sensor elements for a range of focus plane positions, and
transforming the in-focus data into 3D coordinates.

Furthermore, disclosed herein is a method a method for obtaining and/or measuring a 3D geometry of at least a part of a surface of an object, said method comprising:
 generating a probe light by means of a first means for generating probe light,
 transmitting the probe light rays towards the object thereby illuminating at least a part of the object,
 transmitting light rays returned from the object to an array of sensor elements in a first camera,
 imaging with a first depth of field on the first camera at least part of the transmitted light rays returned from the object to the array of sensor elements by means of a first optical system,
 varying the position of the focus plane on the object,
 obtaining at least one image from said array of sensor elements,
 determining the in-focus position(s) of:
  each of a plurality of the sensor elements for a range of focus plane positions, or
  each of a plurality of groups of the sensor elements for a range of focus plane positions, and
 transforming the in-focus data into 3D coordinates,
 selecting a portion of light rays returned from the object, where the light rays have been transmitted through at least a part of the first optical system; and
 capturing at least some of the selected light rays with a second depth of field substantially larger than the first depth of field by means of a second camera.

Furthermore, disclosed herein is a method for obtaining and/or measuring a 3D geometry of at least a part of a surface of an object, said method comprising:
 generating a probe light by means of a first means for generating probe light,
 transmitting the probe light rays towards the object thereby illuminating at least a part of the object,
 transmitting light rays returned from the object to an array of sensor elements in a first camera,
 imaging with a first depth of field on the first camera at least part of the transmitted light rays returned from the object to the array of sensor elements by means of a first optical system,
 varying the position of the focus plane on the object,
 obtaining at least one image from said array of sensor elements,
 determining the in-focus position(s) of:
  each of a plurality of the sensor elements for a range of focus plane positions, or
  each of a plurality of groups of the sensor elements for a range of focus plane positions, and
 transforming the in-focus data into 3D coordinates,
wherein the method further comprises performing spectral analysis of the light returned from the object.

Furthermore, disclosed herein is a method for obtaining and/or measuring a 3D geometry of at least a part of a surface of an object, said method comprising:
 generating a probe light by means of a first means for generating probe light,
 transmitting the probe light rays towards the object thereby illuminating at least a part of the object,
 transmitting light rays returned from the object to an array of sensor elements in a first camera,
 imaging with a first depth of field on the first camera at least part of the transmitted light rays returned from the object to the array of sensor elements by means of a first optical system,
 varying the position of the focus plane on the object,
 obtaining at least one image from said array of sensor elements,
 determining the in-focus position(s) of:
  each of a plurality of the sensor elements for a range of focus plane positions, or
  each of a plurality of groups of the sensor elements for a range of focus plane positions, and
 transforming the in-focus data into 3D coordinates,
wherein the method further comprises performing a color measurement by means of a color measuring probe rigidly attached to the 3D scanner.

Furthermore, disclosed herein is a method for obtaining and/or measuring a 3D geometry of at least a part of a surface of an object, said method comprising:
 generating a probe light by means of a first means for generating probe light,
 transmitting the probe light rays towards the object thereby illuminating at least a part of the object,
 transmitting light rays returned from the object to an array of sensor elements in a first camera,
 imaging with a first depth of field on the first camera at least part of the transmitted light rays returned from the object to the array of sensor elements by means of a first optical system,
 varying the position of the focus plane on the object,
 obtaining at least one image from said array of sensor elements,
 determining the in-focus position(s) of:
  each of a plurality of the sensor elements for a range of focus plane positions, or
  each of a plurality of groups of the sensor elements for a range of focus plane positions, and
 transforming the in-focus data into 3D coordinates,
wherein the method further comprises providing that at least two different perspective views on the acquired images is obtainable without performing movement of the scanner by means of at least one reflective optical element arranged in the scanner.

Furthermore, disclosed herein is an optical system for obtaining and/or measuring a 3D geometry of at least a part of a surface of an object, said optical system comprising:
 a first camera comprising an array of sensor elements,
 a first means for generating a probe light,
 means for transmitting the probe light rays towards the object thereby illuminating at least a part of the object,
 means for transmitting light rays returned from the object to the array of sensor elements,
 a first optical system for imaging with a first depth of field on the first camera at least part of the transmitted light rays returned from the object to the array of sensor elements,
 means for varying the position of the focus plane on the object,
 means for obtaining at least one image from said array of sensor elements,
 means for determining the in-focus position(s) of:
  each of a plurality of the sensor elements for a range of focus plane positions, or
  each of a plurality of groups of the sensor elements for a range of focus plane positions, and
 means for transforming the in-focus data into 3D coordinates.

Disclosed is a scanner for obtaining and/or measuring a 3D geometry of at least a part of a surface of an object, said scanner comprising:
a light first source configured for generating a probe light;
a first camera comprising an array of sensor elements, where said camera is configured for obtaining at least one image from said array of sensor elements;
an arrangement of optical components configured for:
transmitting the probe light rays towards the object such that at least a part of the object can be illuminated;
transmitting light rays returned from the object to the array of sensor elements; and
imaging with a first depth of field at least part of the transmitted light rays returned from the object onto the array of sensor elements;
where the arrangement of optical components comprises focusing optics that defines a focus plane for the scanner,
a positioning device configured for varying the position of the focusing optics, such that the position of the focus plane relative to the scanner is changed,
a data processing device, configured for
determining the in-focus position(s) of:
each of a plurality of the sensor elements for a range of focus plane positions, or
each of a plurality of groups of the sensor elements for a range of focus plane positions,
and for transforming the in-focus data into 3D coordinates.
In some embodiments, the scanner comprises:
optics for selecting a portion of light rays returned from the object, and
a second camera arranged to capture at least some of the selected light rays, where the second camera is configured for obtaining a second depth of field image with a second depth of field which is substantially larger than the first depth of field.
In some embodiments, the scanner comprises:
optics for selecting a portion of light rays returned from the object;
a second camera arranged to capture at least some of the selected light rays; and
optical components arranged to image at least part of the selected portion of the light rays returned from the object onto the second camera with a second depth of field which is substantially larger than the first depth of field.
The positioning device configured for varying the position of the focusing optics allows for a change of the position of the focus plane on the object while maintaining the relative positions of the scanner and the object.
Disclosed is a scanner for obtaining and/or measuring a 3D geometry of at least a part of a surface of an object arranged in a scan volume, said scanner comprising:
a light first source configured for generating a probe light;
a first camera comprising an array of sensor elements, where said camera is configured for obtaining at least one image from said array of sensor elements;
an arrangement of optical components configured for
transmitting the probe light rays towards the scan volume such that at least part of an object arranged in said scan volume can be illuminated;
transmitting light rays returned from the scan volume to the array of sensor elements; and
imaging with a first depth of field at least part of the transmitted light rays returned from the scan volume onto the array of sensor elements;
where the arrangement of optical components comprises focusing optics that defines a focus plane for the scanner, and where the focus plane is located in said scan volume;
a positioning device configured for varying the position of the focusing optics, such that the position of the focus plane is scanned though said scan volume;
a data processing device, configured for
determining the in-focus position(s) of:
each of a plurality of the sensor elements for a range of focus plane positions, or
each of a plurality of groups of the sensor elements for a range of focus plane positions,
and for transforming the in-focus data into 3D coordinates.

When the object and the scanner are arranged relative to each other such that at least part of the object is within said scan volume, the position of the focus plane on the object may be changed when the focus plane is scanned through the scan volume.

In some embodiments, the scan volume is the volume which is scanned when the focusing optics is moved between its outermost positions while maintaining a substantially constant position of the scanner.

In some embodiments, the scan volume is the volume spanned by the focus plane between its outermost positions relative to the scanner while maintaining a substantially constant position of the scanner.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

In some embodiments, the focusing optics is part of the first optical system. The focusing optics may be a lens in a lens system.

In some embodiments, the position of the focus plane is varied on the object by varying the position of the focusing optics in the scanner, such as varying the position relative to other parts of the scanner, such as relative to the casing of the scanner. The means for varying the focusing optics may hence also vary the position of the focus plane on the object.

In some embodiments, the means for varying the position of the focusing optics and hence the focus plane on the object comprises a positioning device, such as a translation stage, for adjusting and controlling the position of the focusing optics. By translating the focusing optics back and forth along the optical axis of the first optical system, the position of the focus plane relative to the scanner may be varied. The position of the focus plane over a scanned object can hence be moved without moving the scanner relative to the object.

Identified in-focus position(s) for sensor elements or groups of sensor elements can be related to 3D coordinates by ray tracing through the first optical system. Such ray tracing may require that the parameters of the first optical system are known. Such knowledge can be obtained by a calibration, such as calibration in which images of an object of known geometry are recorded for a plurality of in-focus positions. Such an object may be a planar checkerboard pattern. Then, the scanner can be calibrated by generating simulated ray traced images of the calibration object and adjusting first optical system parameters as to minimize the difference between simulated and recorded images.

With knowledge of the parameters of the first optical system, one can employ backward ray tracing technique to estimate the 2D→3D mapping. This requires that the scanner's first optical system be known, preferably through calibration. The following steps can be performed:

1. Trace a certain number of rays from each sensor element, starting from the array of sensor elements and through the first optical system (backward ray tracing).

2. Calculate the point where all the traced rays from the sensor element substantially intersect, i.e. the focus point for the sensor element. This point represents the 3D coordinate where a portion of an imaged object will be in focus for this sensor element.

3. Generate a look up table for all the sensor elements with their corresponding 3D coordinates.

The above steps are repeated for a number of different positions of the focusing optical covering the scanner's operation range.

The method may also be performed in the case where the sensor elements are combined in groups of sensor elements.

In some embodiments, the means for determining the in-focus positions comprises a data processing device, such as a computer or a microprocessor. The determining may utilize computer implemented algorithms implemented in a computer program product tangibly embodied in a machine-readable storage device for execution by a programmable processor.

In some embodiments, the means for transforming the in-focus data into 3D coordinates comprises a data processing device, such as a computer or a microprocessor. The transforming may utilize computer implemented algorithms implemented in a computer program product tangibly embodied in a machine-readable storage device for execution by a programmable processor.

The in-focus positions may be determined using the same data processing device which is used for transforming the in-focus data into 3D coordinates, or the determining and the transforming may be carried out using two separate data processing devices.

In some embodiments, the first means for generating a probe light comprises a light first source, such as a monochromatic light source, a semi-monochromatic light source, or a broadband source light source providing light over a wavelength range.

In some embodiments, the first light source is an ultraviolet light source, an infra-red light source and/or a light source emitting in the visible part of the electromagnetic spectrum.

A broadband source may be configured for providing light substantially at all wavelengths in the wavelength range, such as to provide light in a substantially continuous wavelength range. In some embodiments, the broadband source emits white light, i.e. the wavelength range covers substantially the entire range of wavelengths in within the visible part of the electromagnetic spectrum.

Pseudo-broadband light can also be generated by combining a number of monochromatic or semi-monochromatic light sources with wavelengths distributed over the range of wavelengths. The first light source may comprise at least three monochromatic light sources with wavelengths distributed across the visible part of the electromagnetic spectrum. I.e. a probe light of different colors may be provided by at least three monochromatic or narrow-band light sources, such as lasers or LED's, said light sources having wavelengths distributed across the visible part of the wavelength spectrum. This will in general also require means for merging said light sources, such as suitable coated plates.

When the first light source is configured for emitting light over a range of wavelengths, color information can be obtained from the object.

In some embodiments, the means for obtaining at least one image from said array of sensor elements comprises electronic devices configured for converting signals from the array of sensor elements into an image.

In some embodiments, the scanner comprises a nontransitory computer readable medium having one or more computer instructions stored thereon, where said computer instructions comprises instructions for carrying out a method of measuring of a 3D geometry of at least a part of a surface of an object.

Disclosed is a scanner system comprising
  a focus scanning apparatus according to the present invention; and
  a data processing device comprising a nontransitory computer readable medium having one or more computer instructions stored thereon, where said computer instructions comprises instructions for carrying out a method of the present invention.

DEFINITIONS

Optical axis: the optical axis of an optical system is the axis defined by a straight line through the light source, the optics and the lenses in this optical system.

Optical path: the path of the light from the light source to the object and back to the camera. The optical path may change direction, e.g. by means of beam splitter and folding optics.

Optical system: Arrangement of one or more optical components. Optical component could be, but is not limited to: Optical lenses, mirrors, gratings, polarizers, retardation plates, filters, beam splitters.

Image/imaging: An image can be viewed as a 1D or 2D array of values, when obtained with a digital camera, or in optics, a 1D or 2D image indicates that there exists a relation between an imaged curve/surface and an image curve/surface where light rays emerging from one point on said imaged curve/surface substantially converge on one point on said image curve/surface.

Depth of field (DoF): In imaging the convergence of rays from one point in an imaged curve/surface onto the image curve/surface is best obtained for one particular imaged curve/surface. Light emitted from other curves/surfaces in front of or behind the imaged surface does not converge to form images on the image surface to the same degree. In practice, however, light rays from surfaces in front of and behind the image surface may still converge to form acceptable images on the imaged surface. The DoF is the distance along this depth direction where it is possible to form acceptable images.

Perspective: A perspective of an image is specified by the position and orientation of the camera when the picture was taken. If two cameras have a fixed perspective with respect to each other it implies that they move in rigid synchronization to each other.

Aperture: The aperture of an optical system is the opening in the optical system that determines the cone angle of a bundle of rays that come to a focus in the image plane. The aperture can be a plate with a hole in it, it can also be a lens or another optical component.

Downstream: Direction from light source towards object being scanned.

Upstream: Opposite direction of downstream.

3D real world coordinates and/or 3D geometry: 3D real world coordinates and/or 3D geometry is based on a 3D representation, i.e. a 3D digital representation, which can be either point clouds, surface, such as faceted/meshed, or volumetric. A 3D model, i.e. a 3D digital model, can be generated from a 3D representation. Faceted/meshed representations can be generated from point clouds, for example by triangulation. Volumetric models can be obtained with a scanner applying penetrating radiation, such as CT scanners.

BRIEF DESCRIPTION OF THE DRAWINGS

The above and/or additional objectives, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
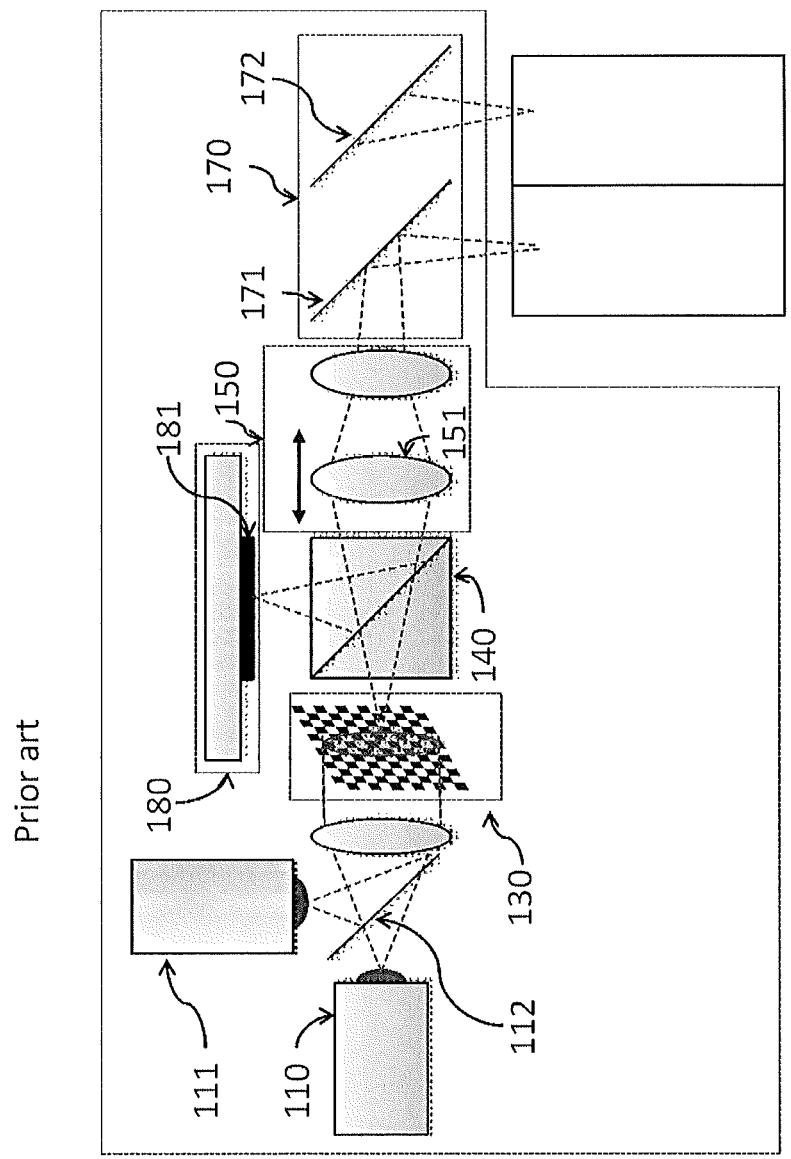
FIG. 1 shows an example of a prior art focus scanning apparatus.

FIG. 1 shows an example of a prior art focus scanning apparatus.

The prior art scanner is a hand-held scanner with all components inside the housing (head). The scanner head comprises a tip which can be entered into a cavity, a light source 110, optics to collect the light from the light source, pattern generation means 130, a beam splitter 140, an image sensor and electronics 180, a lens system which transmits and images the light between the pattern, the object being scanned, and the image sensor (camera) 180. The light from the light source 110 travels back and forth through the optical system 150. During this passage the optical system images the pattern 130 onto the object being scanned and further images the object being scanned onto the image sensor 181. The lens system includes a focusing element 151 which can be adjusted to shift the focal imaging plane of the pattern on the probed object. One way to embody the focusing element is to physically move a single lens element back and forth along the optical axis. The device may include polarization optics. The device may include folding optics 170 which directs the light out of the device in a direction different to the optical axis of the lens system, e.g. in a direction perpendicular to the optical axis of the lens system. As a whole, the optical system provides an imaging of the pattern onto the object being probed and from the object being probed to the camera. One application of the device could be for determining the 3D structure of teeth in the oral cavity. Another application could be for determining the 3D shape of the ear canal and the external part of the ear.

The optical axis in FIG. 1 is the axis defined by a straight line through the light source 110, optics and the lenses in the optical system 150. This also corresponds to the longitudinal axis of the scanner illustrated in FIG. 1. The optical path is the path of the light from the light source 110 to the object and back to the camera 180. The optical path may change direction, e.g. by means of beam splitter 140 and folding optics 170.

The focus scanning apparatus comprises a flat scan tip with large scan length, using a plurality of, e.g. dichroic, mirrors and light sources.

The configuration of the focus scanning apparatus allows for a scan tip with a smaller height than the scan length. The light from two sources 110 and 111 emitting light of different colors/wavelengths is merged together using a suitably coated plate, e.g. a dichroic filter, 112 that transmits the light from light source 110 and reflects the light from light source 111. At the scan tip a suitably coated plate, e.g. a dichroic filter, 171 reflects the light from one source onto the object and transmits the light from the other source to a mirror at the end of the scan tip 172. During scanning the focus position is moved such that the light from light source 110 is used to project an image of the pattern to a position below 171 while light source 111 is switched off. The 3D surface of the object in the region below 171 is recorded. Then light source 110 is switched off and light source 111 is switched on and the focus position is moved such that the light from light source 111 is used to project an image of the pattern to a position below 172. The 3D surface of the object in the region below 172 is recorded. The region covered with the light from light sources 110 and 111 respectively may partially overlap.

Figure 2:
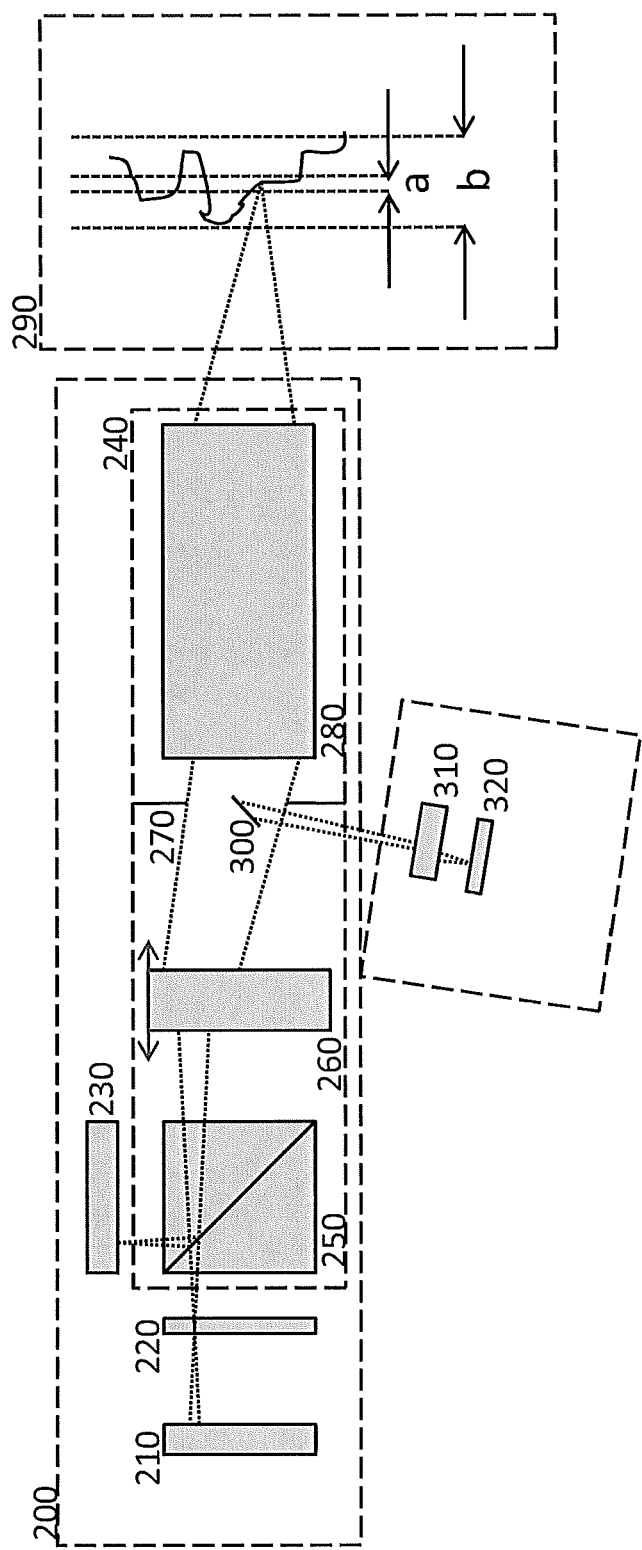
FIG. 2 shows an example of a focus scanning apparatus comprising a second camera.

FIG. 2 shows an example of a focus scanning apparatus comprising a second camera.

The focus scanning apparatus 200 comprises a light source 210 that may comprise collimation optics, a pattern 220, a first camera 230, a first optical system 240 comprising a beam splitter 250 that may be polarizing, focusing optics 260, an aperture 270, and other optical elements 280. The focus scanning apparatus is aimed at the object being scanned 290. Some light rays emitted from the light source and imaged through the first optical system onto the object being scanned, returned through the first optical system and imaged onto the camera are illustrated as dotted lines. The depth of field a, which is the distance between the arrows, of the image of the object on the first camera 230 is small thanks to a large aperture 270 in the first optical system 240.

Here the optical components of the first optical system, i.e. the beam splitter 250, the focusing optics 260, the aperture 270, and the other optical elements 280, are arranged to both transmit the probe light rays towards the object and to transmit light rays returned from the object to the array of sensor elements. That is, the means for transmitting the probe light rays towards the object thereby illuminating at least a part of the object, and the means for transmitting light rays returned from the object to the array of sensor elements are the same and are part of the first optical system.

During a 3D scan the focus of the first optical system is swept from one end of the focus volume to the other end by adjusting the focusing optics 260 indicated by the double arrow. The focus sweep translates the focus in a direction substantially along the optical axis of the first optical system 240. During the focus sweep a stream of images is obtained with the camera 230. The in-focus regions of the images in the sweep are determined and from this 3D coordinates of at least a part of the object being scanned is determined.

A part of the light returned from the object 290 and transmitted through the other optical elements 280 of the first optical system 240 are reflected by a second optical element 300, such as a small mirror, a beam splitter, a filter etc., placed in the aperture 270. The reflected rays are transmitted to a second optical system 310 and a second camera 320. The second optical system 310 together with the other optical elements 280 forms an image of at least a part of the object 290. The aperture in the optical system comprising the other optical elements 280 and the second optical system 310 can be coincident with the aperture of the first optical system 240. In this case the size of the aperture is determined by the size of the mirror 300. Since this mirror is small then the depth of field of the image on the second camera 320 is larger than the depth of field of the image(s) on the camera 230. In the figure this larger depth of field is denoted b. Since the mirror 300 is small compared to the dimensions of the aperture 270 it is only a small fraction of the light rays returned from the object that are reflected by the mirror. Since the mirror 300 is placed in the aperture of the first optical system 240 the field of view of the first camera 230 is not reduced, i.e. the view to no part of the object is obstructed compared to what could be seen without the small mirror 300. The presence of the small mirror 300 does not substantially affect the 3D scanning. The depth of field of the image on the second camera 320 is preferably so large that all parts of the object being scanned 290 are in focus at the same time. Since in this figure the focusing optics 260 is outside of the light path from the light returned from the object to the second camera, then the image on the second camera is substantially unaffected by the 3D scanning process, which is performed by means of the focusing optics.

The frame rate on the second camera 320 can be different than the frame rate on the first camera 230 and the rate of 3D scanning. It may be preferred that the frame rate on the second camera 320 is higher than the rate of 3D scanning but smaller than the frame rate of the first camera 230. The image from the second camera can be displayed to the operator of the scanner and allow to give a real-time view of the scanned area. This can help the operator in adjusting the relative position and orientation of the scanner and the object being scanned. This can be particularly useful in a handheld scanner.

It is often advantageous to use near-monochromatic light for the 3D scanning. Using near-monochromatic light makes the construction of the first optical system 240 simpler. It may in other words be advantageous to have a near-monochromatic first light source 210. But at the same time it may be advantageous to obtain a color image of the object being scanned with the second camera. A large depth of field image in color may be an advantage if it is an objective to overlay color texture onto the 3D surface or 3D model of the object. A color image could also be an advantage in assistance with aiming the scanner towards the object being scanned. Or a color image could simply give a better user experience when operating the scanner compared to a black-and-white image.

The reference numbers in FIG. 2 are also used to denote corresponding features in the following figures. Likewise, reference numbers in the following figures may also be used to denote corresponding features in the other following figures.

Figure 3:
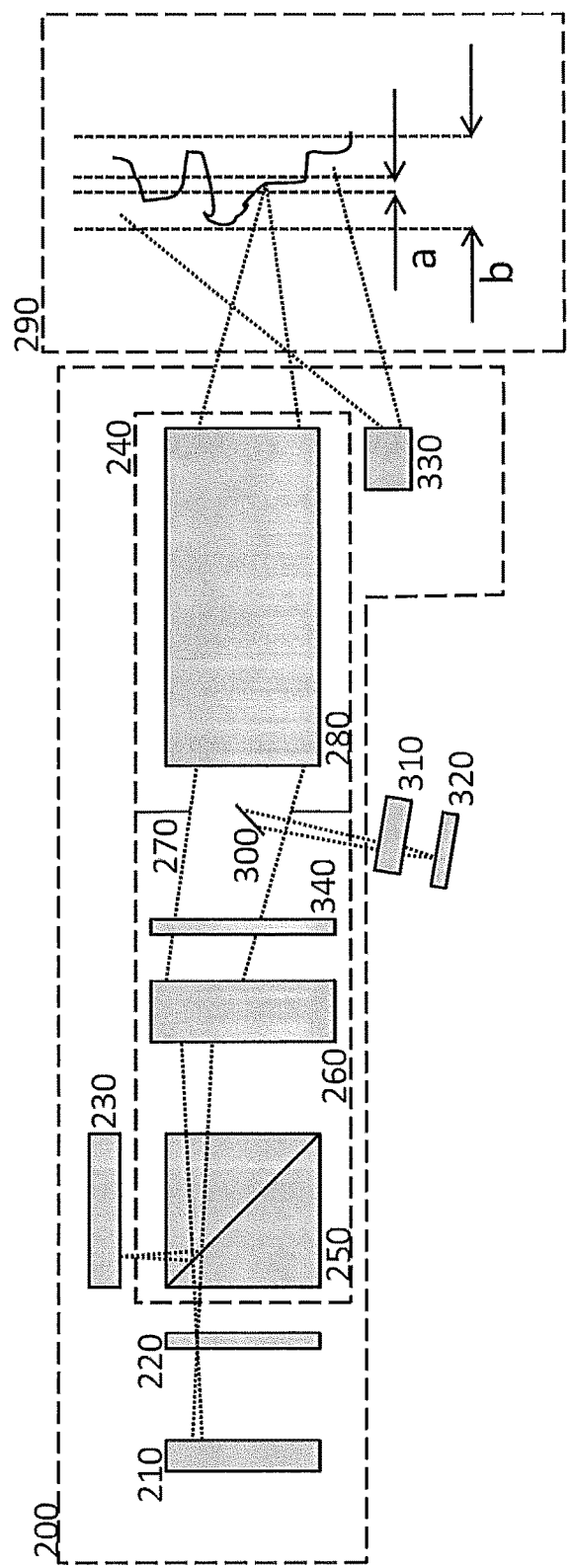
FIG. 3 shows an example of a focus scanning apparatus comprising a second camera capable of producing a color image.

FIG. 3 shows an example of a focus scanning apparatus comprising a second camera capable of producing a color image.

The focus scanning apparatus provides for a color image on the second camera 320 while at the same time using near-monochromatic light for the 3D scanning. This is possible by using a second light source 330 with a different wavelength spectrum than the near-monochromatic first light source 210 together with a color camera. The second light source 330 can preferably be a white-light source and it is understood that the second light source can comprise collimation optics. The white-light illumination may potentially disturb the 3D scanning if the white light is transmitted to the first camera 230. This disturbance may be minimized by having a transmission filter 340 placed in the first optical system 240. This filter should allow transmission of the first light source 210 while diminishing or completely preventing passage of light from the second light source 330. One way to achieve this is to have e.g. an infrared first light source 210 and a white second light source 330 and use a filter 340 that only transmits infrared light. Another way to achieve this is to have a narrow band first light source 210 in the visible range and a white second light source 330 and use a filter 340 that is pass-band to allow transmission of the light from the light source 210 while not allowing transmission of other wavelengths within the visible range. Such a filter would allow transmission of a small fraction of the white light from the second source 330. But this small fraction could be too small to disturb the 3D scanning appreciably. The second camera 320 is in this figure a color camera, and the camera may obtain color images by applying a color filter array such as a Bayer color filter array to a black-and-white sensor. Alternatively the camera could obtain color images by using three sensors and a trichroic beam splitter to split the white-light image into red, green, and blue images.

If a second light source 330 is used then it may be advantageous to have this light source placed so that it illuminates the object 290 with the same perspective as the first light source 210. This is because then all parts of the object being scanned by means of the first light source 210 are also illuminated by the second light source 330.

The figure shows that the second light source is arranged in the scanner proximal to the object being scanned, i.e. the light source is arranged in the end of the scanner which points towards the object being scanned. However, other locations of the second light source inside and outside the scanner may also be possible for obtaining the desired effect as described above.

Figure 4:
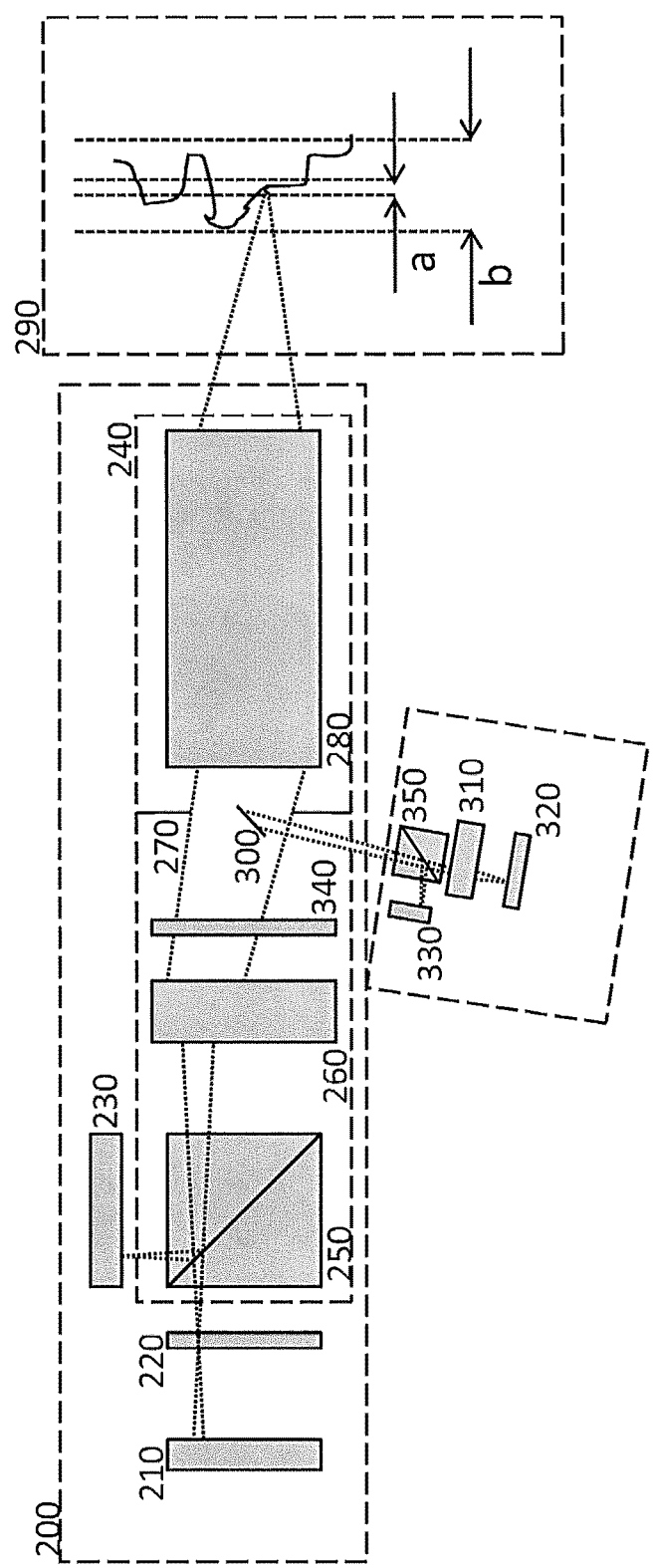
FIG. 4 shows an example of a focus scanning apparatus which provides for illuminating the object being scanned with the same perspective for both the first light source and the second light source.

FIG. 4 shows an example of a focus scanning apparatus which provides for illuminating the object being scanned with the same perspective for both the first light source and the second light source.

The focus scanning apparatus 200 comprises a first light source 210 and a second light source 330 for illuminating the object 290 with the same perspective. This is possible by using a beam splitter 350 that combines the optical path of the second optical system 310 and the second light source 330. The light from the second light source 330 is then by means of the mirror 300 brought to propagate along the optical axis of the first optical system 240 and it is transmitted through a part of the first optical system.

The figure shows that the second light source is arranged near the second optical system. However, other locations of the second light source may also be possible for obtaining the desired effect as described above.

For example it may be advantageous to have the second light source 330 placed in or just outside the aperture 270 of the first optical system 240. This is because when the second light source is so placed then it will illuminate the same portion of the object being scanned as the first light source.

Figure 5:
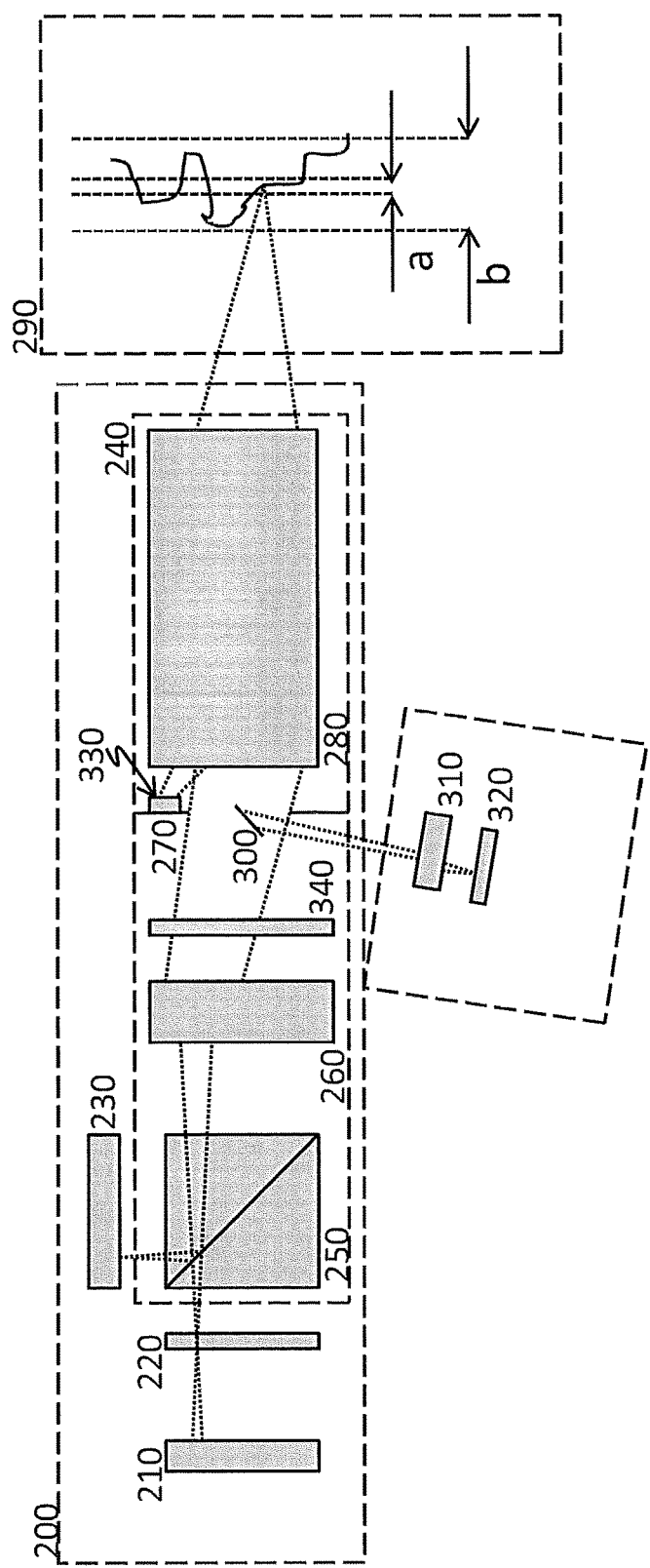
FIG. 5 shows an example of a focus scanning apparatus with a second light source.

FIG. 5 shows an example of a focus scanning apparatus with a second light source.

In the figure, the second light source 330 is placed just outside the aperture 270 of the first optical system 240.

However, other locations of the second light source may also be possible for obtaining the desired effect as described above.

For space considerations it may also be advantageous to place the second light source at a position away from the object being scanned. The light can then be transmitted to the object being scanned by means of one or more wave guides.

Figure 6:
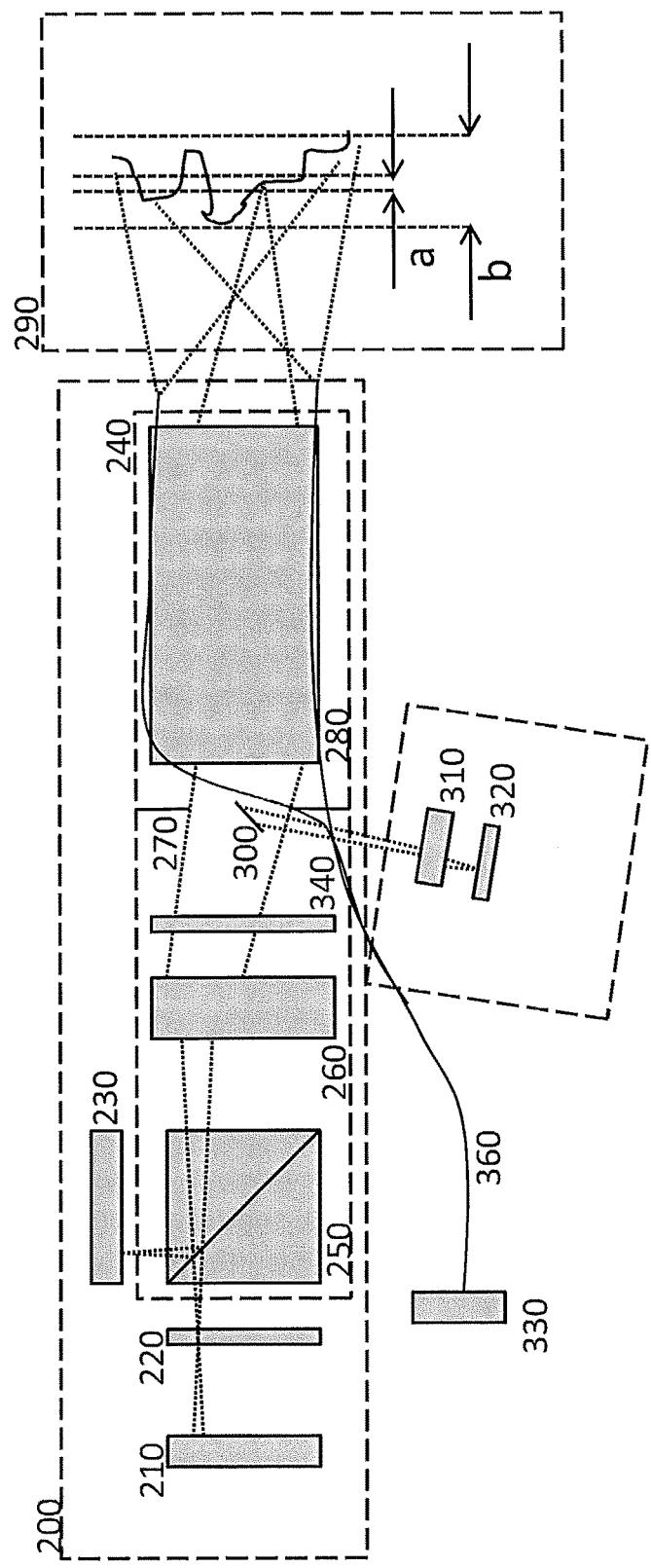
FIG. 6 shows an example of a focus scanning apparatus where the second light source is coupled to a wave guide.

FIG. 6 shows an example of a focus scanning apparatus where the second light source is coupled to a wave guide.

The figure shows that the second light source 330 is coupled to a wave guide 360 that transmits the light to the object being scanned. It is understood that the second light source 330 includes coupling optics to couple the light into the waveguide. The figure shows that the waveguide 360 is split into two so that the light from the second light source 330 is emitted from the end of two waveguides. This is provided to achieve that the illumination of the object becomes more uniform and to ensure that fewer parts of the surface of the object is left in shadow. The waveguide can be split into more than two to make the illumination even more uniform and with even fewer areas in shadow.

It is also possible to have a third, fourth etc. light source to illuminate the object being scanned. If wave guides are used then it may be natural to have one wave guide per light source.

As an alternative to a white light second light source 330 and a color second camera 320 it is possible to have a second light source 330 that emits near-monochromatic light and a black-and-white camera 320 and still obtain color images with large depth of field. One way to do this is to have a second light source 330 that can change color. At different times the light source can emit red, green and blue light. This is possible with a second light source comprising e.g. red, green, and blue LEDs that can be turned on and off at different times. The second light source could then emit red, green, and blue light in sequence. The black and white second camera 320 can then obtain the corresponding red, green, and blue images. These images can then be combined to one full-color image. If the acquisition of the red, green, and blue images is sufficiently fast, then there is substantially no relative motion between the scanner and the object being scanned, even thought the apparatus is hand-held and thus moved, and it is straight-forward to combine the three images into one color image. Sufficiently fast could mean that the three images are acquired within e.g. 1/20 s.

The acquisition of color images with the second camera 320 does not necessarily imply that the camera only records red, green, and blue components of the image. High-precision color analysis may require more than three individual color components. This could be the case for e.g. determination of tooth shade when scanning teeth. The visible spectrum could be covered with a larger set of individual colors. Such detailed color analysis is generalizable from the color image schemes described in the above.

Figure 7:
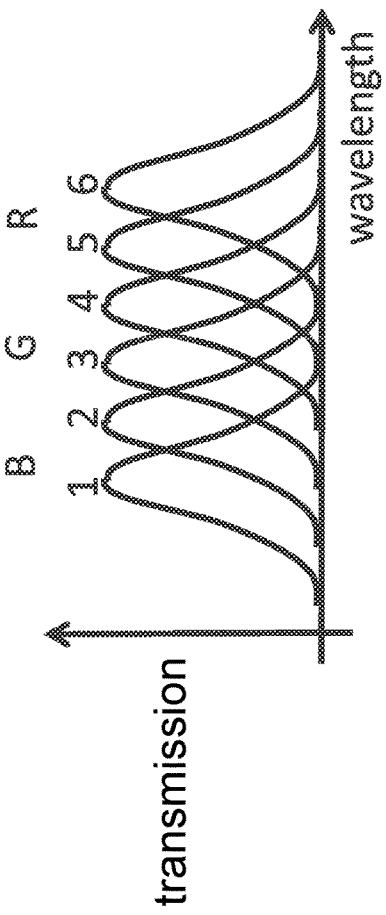
FIGS. 7A and 7B show examples of color filters for use in the second camera.
FIG. 7C shows a schematic illustration of a pass band filter.

FIG. 7 shows examples of color filters for use in the second camera.

FIG. 7a shows one period of a Bayer color filter array for obtaining color images in a camera, which can be used in the second camera and thus in the apparatus. This type of color filter array is well known in the art.

FIG. 7b shows one period of a color filter array with a larger set of individual colors, which can be used in the second camera and thus in the apparatus. Each number corresponds to a color filter with a pass-band transmission schematically indicated in FIG. 7c.

Figure 8:
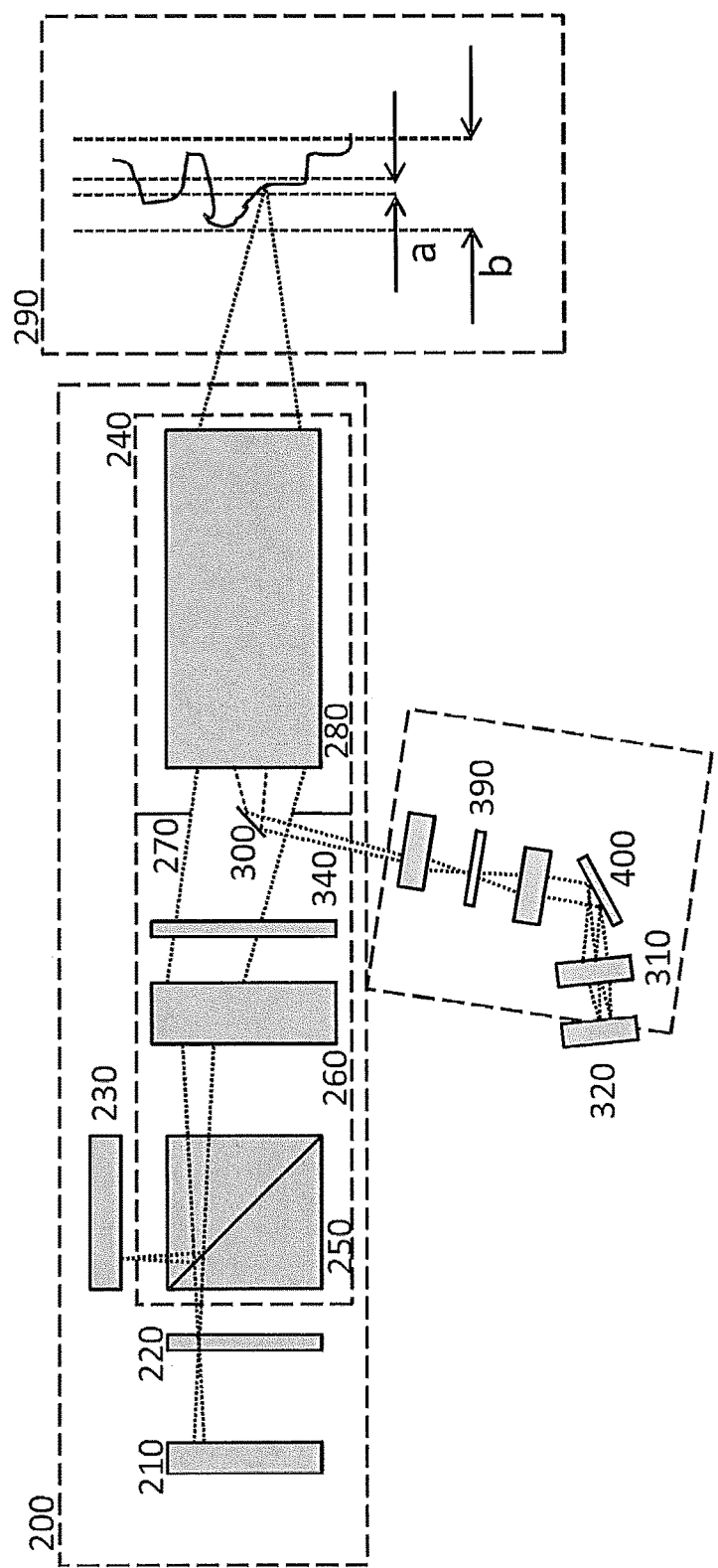
FIG. 8 shows an example of a focus scanning apparatus configured for performing a spectral analysis using a second camera.

FIG. 8 shows an example of a focus scanning apparatus configured for performing a spectral analysis.

Here one dimension of the 2D second camera 320 is used as a spatial dimension while the other dimension of the 2D second camera 320 is used as a spectral dimension. This is achieved in the following way: Light rays are selected by a small second optical element 300, e.g. mirror, in the aperture 270 of the first optical system 240 and imaged onto a slit 390. The slit selects a 1D portion of the image which then is spectrally analyzed by projecting the 1D portion onto a diffractive optical component 400, such as a grating, where the diffractive optical component is arranged to diffract each section of the 1D portion of the image into a plane perpendicular to the 1D portion. Additional optics guides the diffracted light rays onto the 2D sensor array in the second camera 320 such that it obtains a spectrum for each portion of the 1D portion of the image. In this case the second light source can preferably be a white-light source, and it is understood that the second light source can comprise collimation optics.

Figure 9:
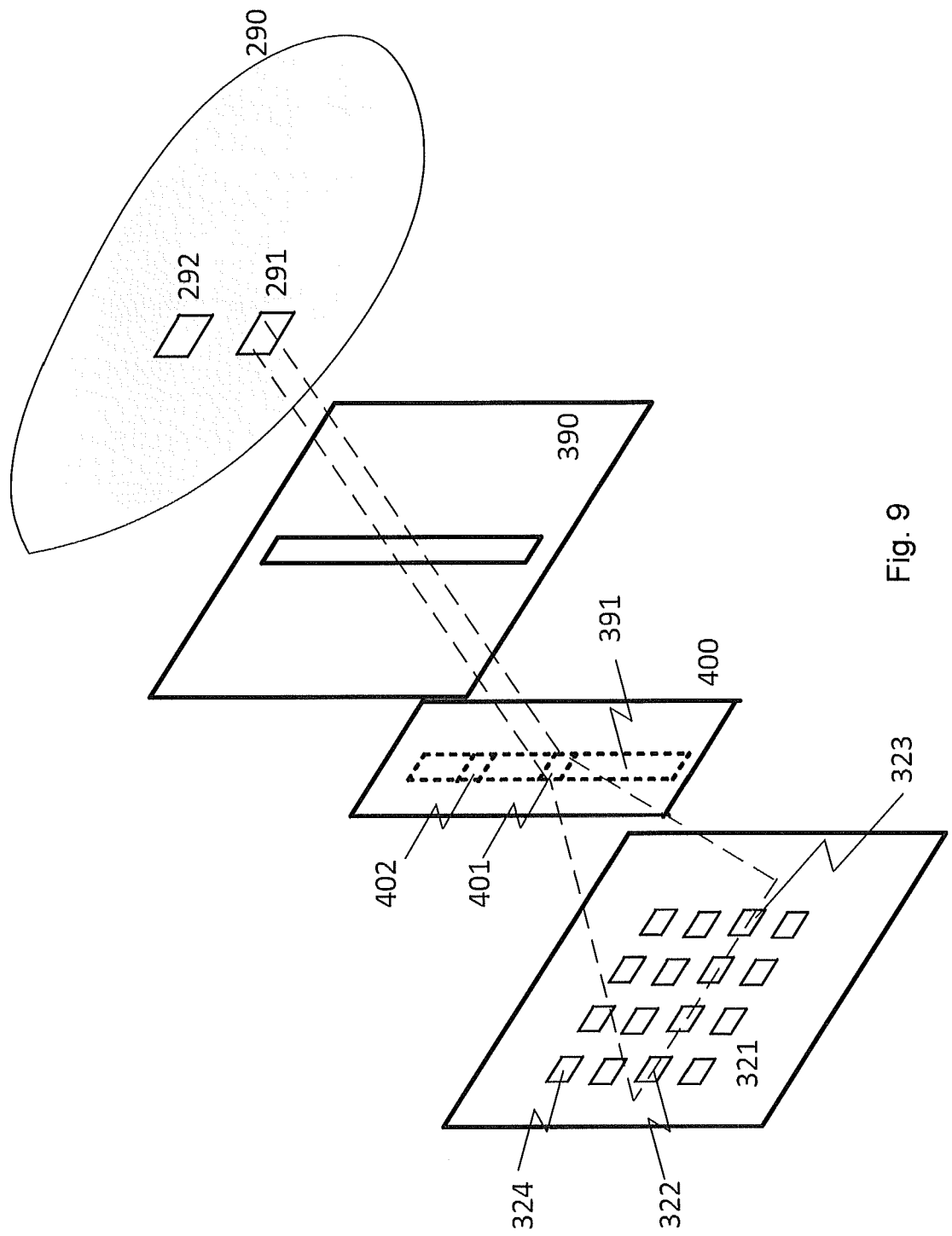
FIG. 9 shows an example on how the second camera may be used for spectral analysis.

FIG. 9 shows an example on how the second camera may be used for spectral analysis.

A portion of the light rays returning from the object 290 are selected by the second optical element and imaged onto a slit 390 which then selects a 1D portion 391 of the 2D distribution of the light rays. The 1D portion 391 is then projected onto a diffractive optical component 400, such as a grating, where the diffractive optical component 400 is arranged to diffract each section 401, 402 of the 1D portion 391 into a plane perpendicular to the longitudinal axis of the 1D portion 391. Additional optics may be arranged to guide the diffracted light rays onto the 2D array of sensor elements 321 in the second camera such that different colors of the light in one section is diffracted into a wavelength specific angle and hence onto a wavelength specific sensor element. There is hence a correlation between each sensor element in the array of sensor elements and the wavelength of light rays in a section of the selected 1D portion. From knowledge of this correlation, obtained e.g. by a prior calibration of the scanner, a spectrum can be obtained for each section 401, 402 of the 1D portion 391. A light ray received by sensor elements 322 is hence originating from the same portion 291 of object 290 as the light ray received by sensor element 323, but has a different wavelength. On the other hand the light ray received by sensor element 324 has the same wavelength as the light ray received in sensor element 322 but originates from a different portion 292 of the object 290. When scanning the object by moving the scanner relative to the object, the surface can be scanned to obtain both spatial and texture information.

The geometrical data obtained from the 1D portion may also be used for registration of the color data into a previously obtained 3D model of the object.

In this scanner embodiment, the second light source should preferably be a broadband source, such as a white-light source. It is understood that the second light source can comprise collimation optics.

This embodiment hence provides that one dimension of the second camera is used to obtain information relating to the spatial properties of the object, while the other dimension of the second camera is used for obtaining spectra information.

Figure 10:
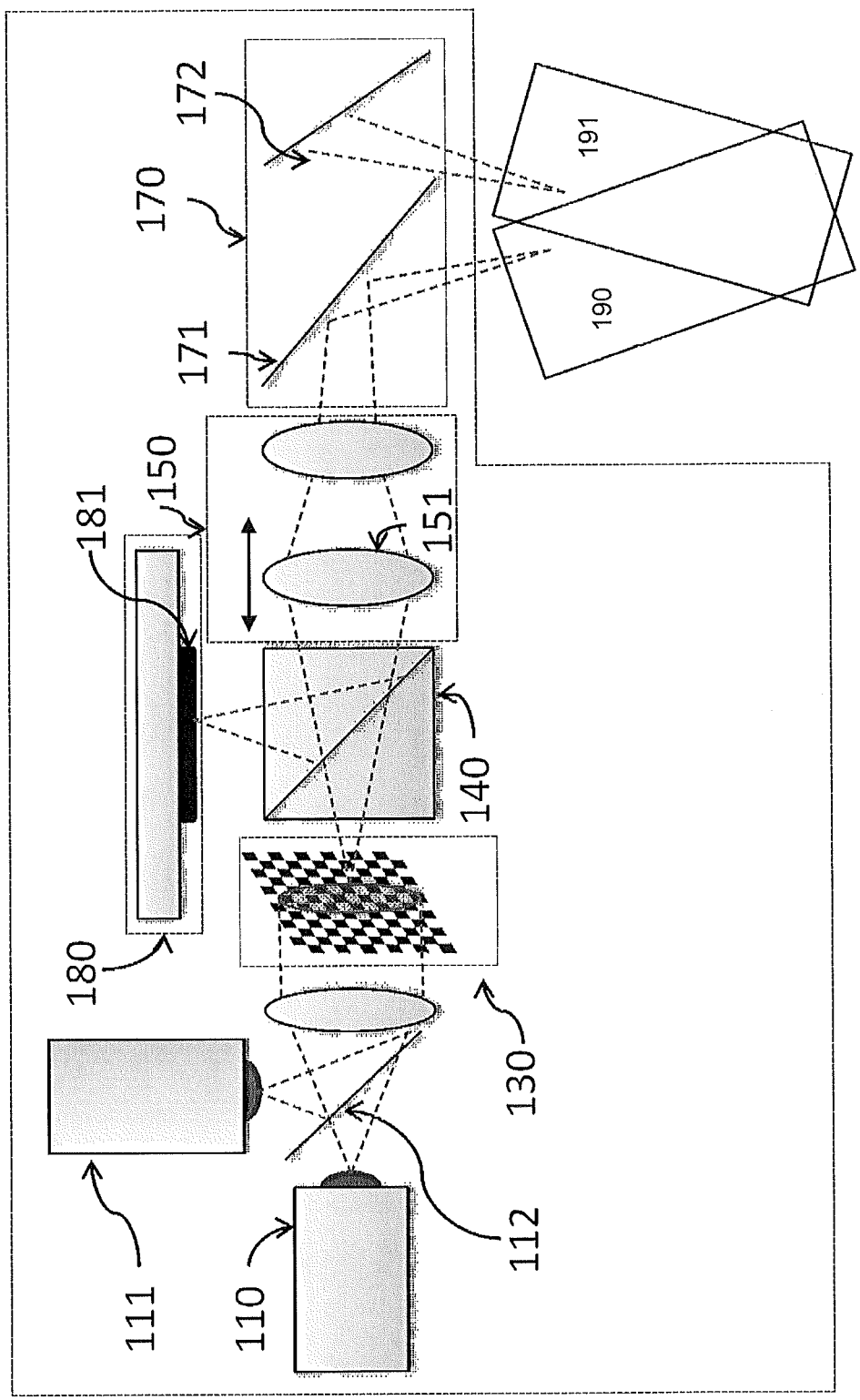
FIG. 10 shows an example of a focus scanning apparatus which enables the object being scanned to be seen from two different perspectives in the scanning.

FIG. 10 shows an example of a focus scanning apparatus which enables the object being scanned to be seen from two different perspectives in the scanning.

The light from two light sources 110 and 111 emitting light of different colors/wavelengths is merged together using a suitably coated plate 112, e.g. a dichroic filter that transmits the light from light source 110 and reflects the light from light source 111. At the scan tip a suitably coated plate 171, e.g. a dichroic filter, reflects the light from one light source onto the object and transmits the light from the other light source to a filter or mirror 172 at the end of the scan tip.

During scanning the focus position is moved by means of the focus lens 151, such that the light from light source 110 is used to project an image of the pattern to a position below 171 while 111 is switched off. The 3D surface of the object in the region below 171 is recorded. Then light source 110 is switched off and light source 111 is switched on and the focus position is moved such that the light from light source 111 is used to project an image of the pattern to a position below 172. The 3D surface of the object in the region below 172 is recorded. The region covered with the light from light sources 110 and 111 respectively may partially overlap.

In this example, the dichroic filters or mirrors 171 and the mirror 172 are purposely put at an angle with respect to each other. This means that the scan volumes 190 and 191 below the filters or mirrors 171 and 172 have an overlap, and the object being scanned is thus seen from two different perspectives in these volumes 190, 191. Together the dichroic filters or mirrors 171 and the mirror 172 act as a reflective optical element which provides that two different perspective views on the acquired images can be obtained without moving the scanner relative to the object.

Figure 11:
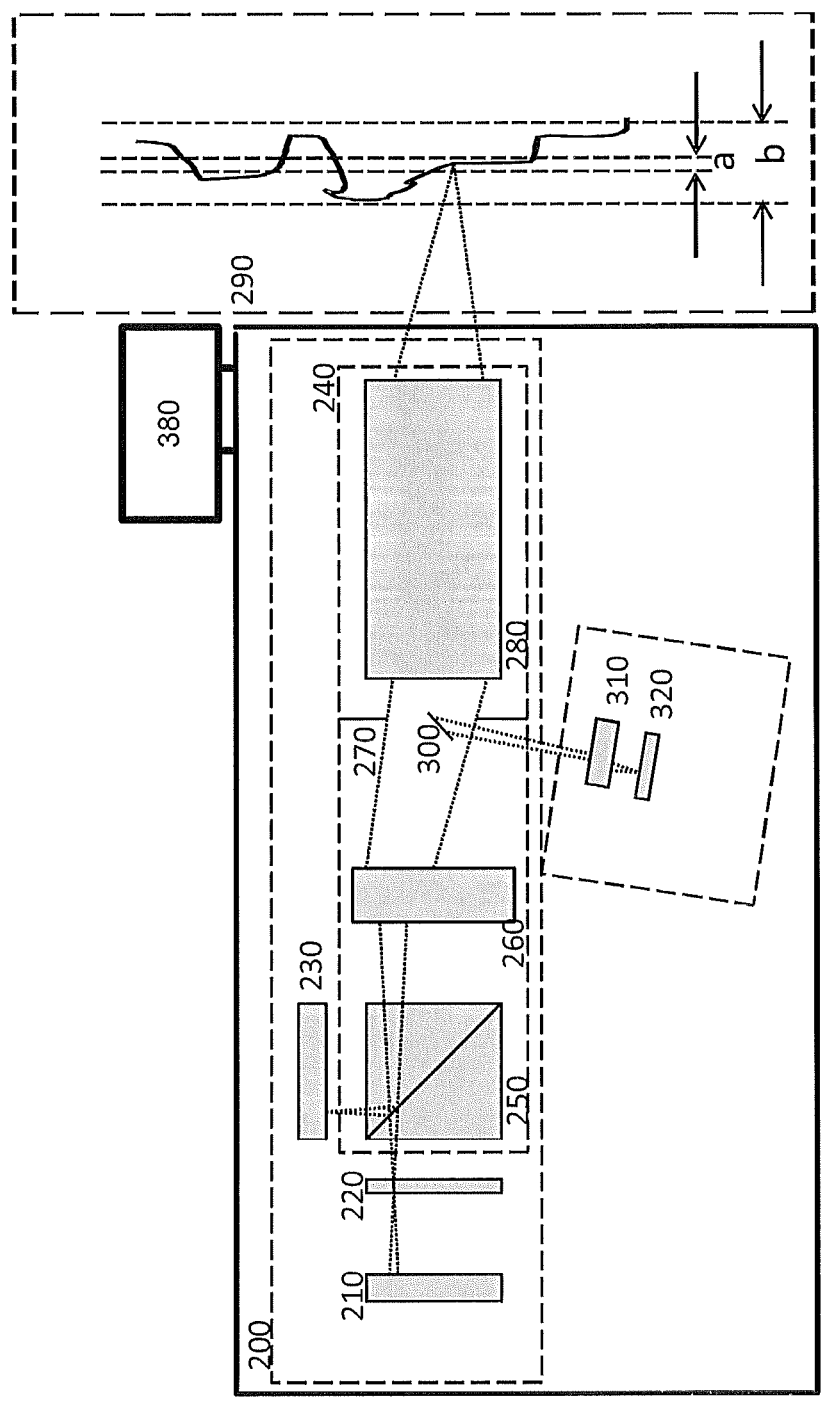
FIG. 11 shows an example of a focus scanning apparatus with a color measurement probe.

FIG. 11 shows an example of a focus scanning apparatus with a color measurement probe.

The scanner 200 comprises a color measuring probe 380 rigidly attached to the 3D scanner.

The color measuring probe 380 is arranged such that it is suitable for measuring the shades of the object 290, e.g. tooth, which the focus scanning optics are obtaining the 3D geometry of.

The color measuring probe 380 is configured to perform the color measurement in at least one point on a tooth. In some cases the color may be measured in e.g. two points or more on a tooth. The color of a tooth may be different along its length due to e.g. different thickness of the tooth.

The position of the point measurement and/or the orientation of the color measurement probe 380 relative to the object 290 is derivable due to the rigid attachment of the color measuring probe 380 relative to the scanner 200.

The color measuring probe 380 may be arranged perpendicularly to a surface of the object 290.

The color measuring probe 380 may comprises a probe tip including one or more light sources and a plurality of light receivers, spectrometer system(s) for measuring the color of the object, a processor for processing the measured data etc.

In the figure the color measuring probe is shown to be arranged in top on the scanner. However, the probe may be arranged anywhere suitable on or in the scanner, such as on the side, below, in the front, in the back etc.

Figure 12:
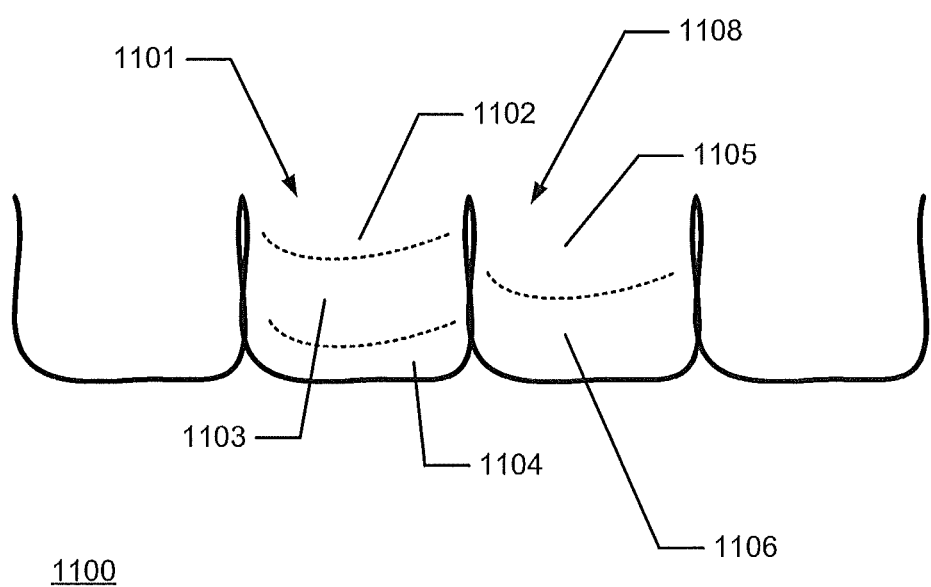
FIG. 12 shows an example of a set of teeth with regions of different color.

FIG. 12 shows an example of a set of teeth with regions of different color. The set of teeth 1100 comprises a number of teeth, e.g. the upper front teeth. The teeth may be color measured with a color measuring probe, see FIG. 10. The color measurement shows that the tooth 1101 comprises three different color regions, where color region 1102 is the region closest to the gingival, and this region may have the color A5. The region 1103 is the center region of the tooth 1101 and this region may have the color A6. The region 1104 is the region closest to the incisal edge of the tooth and this region may have the color A7.

The color measurement further shows that the tooth 1108 comprises two different color regions, where color region 1105 is the region closest to the gingival, and this region may have the color A6. The region 1106 is the region closest to the incisal edge of the tooth and this region may have the color A7.

The color codes A5, A6, and A7 are randomly chosen and may not have any relation to real color codes of teeth.

Figure 13:
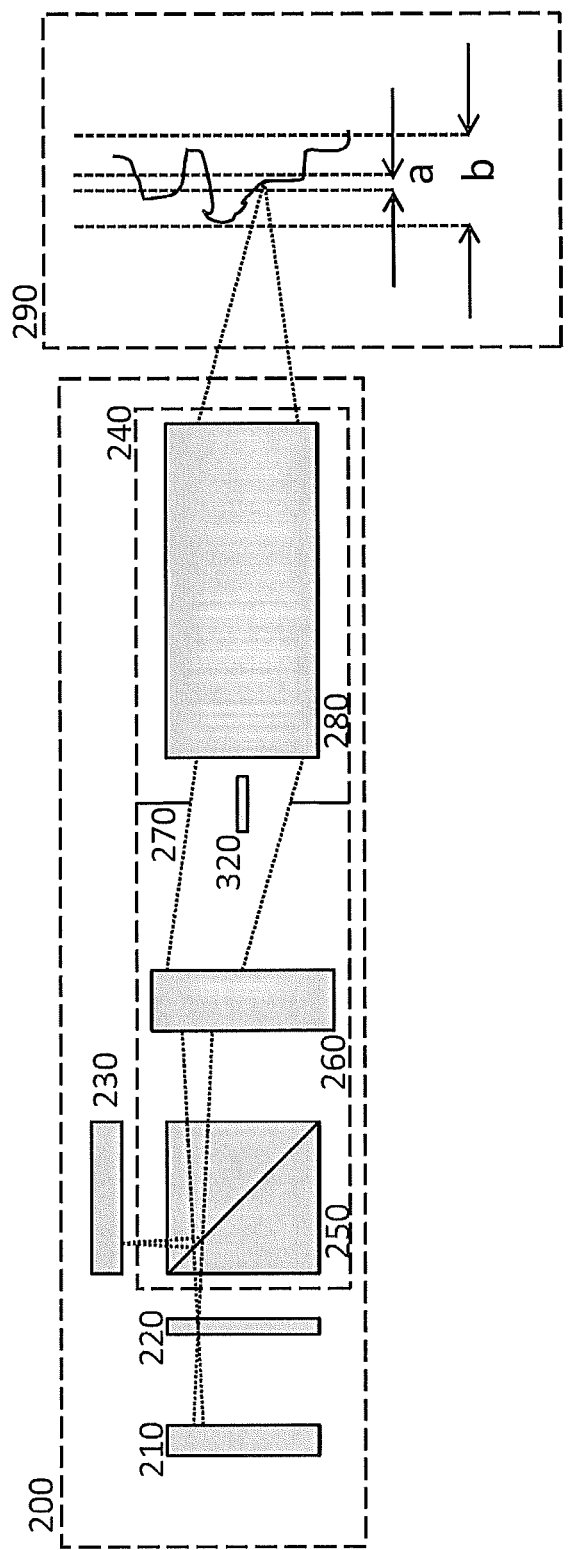
FIG. 13 shows an example of a focus scanning apparatus comprising a miniature second camera arranged in the aperture.

FIG. 13 shows an example of a focus scanning apparatus comprising a miniature second camera arranged in the aperture.

Instead of having a mirror 300 placed in the aperture 270 to reflect a part of the light returned from the object 290 and transmitted through the other optical elements 280, the second camera 320 is here a miniature camera arranged in the aperture 270.

Since the second camera 320 is small compared to the dimensions of the aperture 270 when using a miniature camera it is only a small fraction of the light rays returned from the object that are collected by the second camera 320. Since the second camera 320 is placed in the aperture of the first optical system 240 the field of view of the first camera 230 is not reduced. The depth of field of the image on the second camera 320 is preferably so large that all parts of the object being scanned 290 are in focus at the same time. One miniature camera which can be used is the NanEye 2B 1 mm 62 k pixels miniature camera provided by AWAIBA. The size of this camera is: 1 mm×1 mm×1.5 mm (W L H). Anther suitable miniature camera is the IntroSpicio™ 120 from Medigus. This video camera has a diameter of 1.2 mm and a length of 5 mm.

Figure 14:
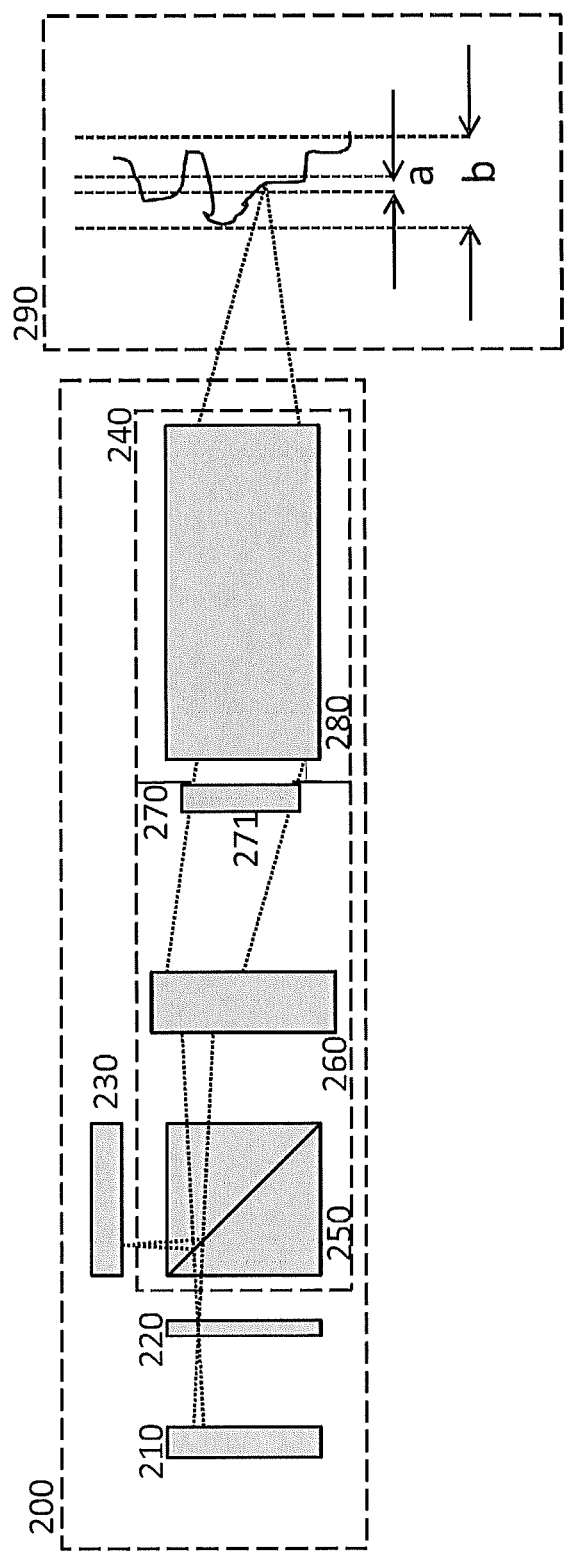
FIG. 14 shows a one camera embodiment capable of obtaining both shallow and large depth of field images.

FIG. 14 shows a single-camera embodiment capable of obtaining both shallow and large depth of field images.

Compared to the embodiment illustrated in FIG. 2, the embodiment of FIG. 14 comprises a first optical element 271 instead of the second optical element, second optical system, and second camera of FIG. 2. The change of the field of depth between a relatively smaller first depth of field and a relatively larger second depth of field on the first camera is provided by a change in the effective area of the aperture 270. The first optical element 271 may be a automatically adjustable iris diaphragm arranged with its center at the optical axis of the focus scanning apparatus. When the aperture of the iris diaphragm is reduced, the depth of field by which the light rays returning from the object are imaged onto the first camera increases.

The first optical element 271 may alone define the aperture 270 such that the two are one integrated component.

FIG. 15 shows the use of a focus scanning apparatus with a color measurement probe attached. Here the color measuring probe 380 is seen as being rigidly attached to the focus scanning apparatus 200 but it could also be an integrated part of the focus scanning apparatus.

Figure 15A:
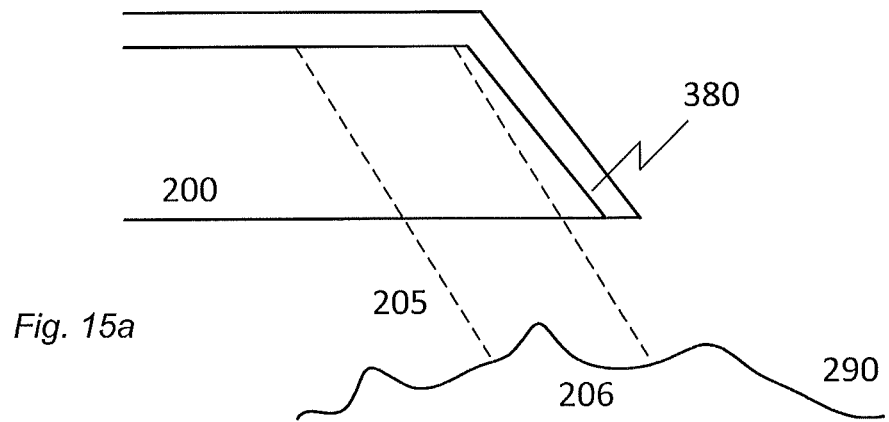
FIG. 15 shows the use of a focus scanning device with a color measurement probe attached.

FIG. 15*a* illustrates how the focus scanning apparatus can be arranged when it is moved relative to the object 290 in order to obtain data for the 3D geometry of a surface of the object. The dotted lines 205 indicate the boundaries of the scan volume of the focus scanning apparatus.

Figure 15B:
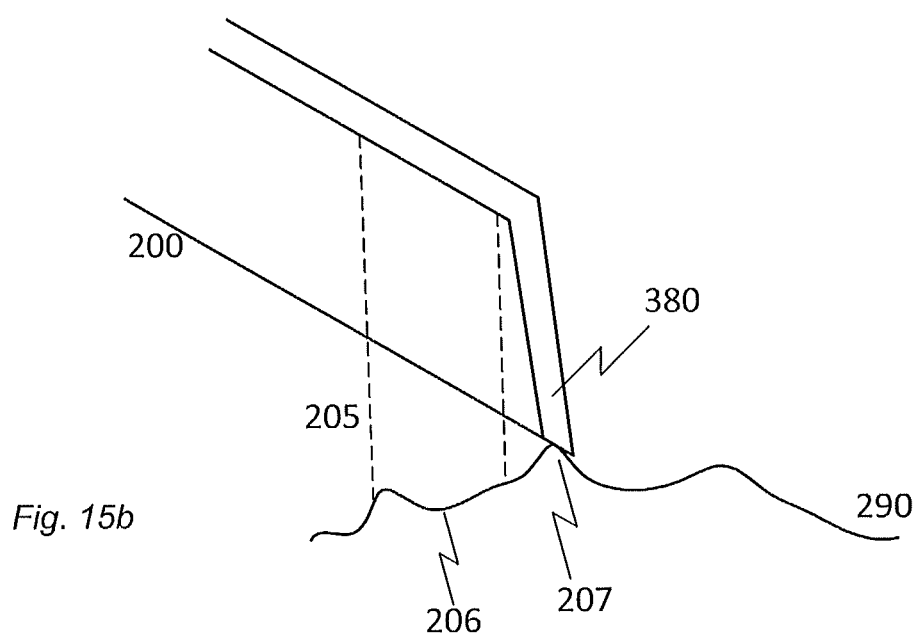

When acquiring data relating to the color of the object 290, the color measuring probe 380 is brought into close proximity with the object surface as illustrated in FIG. 15*b*. The relative arrangement of the color measuring probe 380 and the focus scanning apparatus 200 (or the remaining components of the scanner) is such that the color measuring probe 380 can obtain color data from one section 207 of the object 290 while geometrical data simultaneously can be acquired from another section 206 of the object 290 by the focus scanning optics of the focus scanning apparatus. The geometrical data acquired for a certain color measurement can be used for aligning the measured color with the 3D model derived from the geometrical data obtained with the scanner arranged as seen in FIG. 15*a*. A registration of the color data for one or more sections of the object can then provide that the 3D model of the object is colored according to the true color of the object. The coloring of the 3D model may utilize a smoothing algorithm configured for smoothly changing the color of the object between colors measured at different sections of the object.

The scanning of the surface to obtain the 3D geometry can be performed first such that the 3D geometry is known before the color data are acquired. In this case, the registration of the color data into the 3D model of the object can be performed during the color data acquisition and the color data can be displayed together with the geometrical data. An advantage of this approach is that an operator based on the visualization of the color and geometrical data can determine when he has acquired a sufficient amount of color data.

Alternatively, the color measurement can be performed before the 3D scanning of the object and stored in a memory unit. When the 3D geometry is obtained, the registration of the color data onto the 3D geometry can be performed.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A scanner for obtaining and/or measuring a 3D geometry of at least a part of a surface of an object, said scanner comprising:
   a first light source configured for generating probe light rays;
   a first camera comprising an array of sensor elements, where said first camera is configured for obtaining at least one image from said array of sensor elements;
   an arrangement of optical components configured for:
      transmitting the probe light rays towards the object such that at least a part of the object can be illuminated;
      transmitting light rays returned from the object to the array of sensor elements; and
      imaging with a first depth of field at least part of the transmitted light rays returned from the object onto the array of sensor elements;
   where the arrangement of optical components comprises focusing optics that defines a focus plane for the scanner, and where at least part of the optical components forms a first optical system that provides the imaging of light onto the array of sensor elements;
   a positioning device configured for varying the position of the focusing optics, such that the position of the focus plane relative to the scanner is changed;
   a data processing device, configured for:
      determining the in-focus position(s) of:
         each of a plurality of the sensor elements for a range of focus plane positions, or
         each of a plurality of groups of the sensor elements for a range of focus plane positions,
      and for transforming the in-focus data into 3D coordinates;
   the scanner further comprising:
      optics for selecting a portion of the light rays returned from the object, where the light rays have been transmitted through at least a part of the first optical system, and where the optics for selecting a portion of light rays returned from the object include a second optical element that is arranged in an aperture in the first optical system; and a second camera arranged to capture at least some of the selected light rays to provide a second depth of field image with a second depth of field, or
      a third camera arranged to capture a portion of the light rays returned from the object, where the light rays have been transmitted through at least a part of the first optical system, to provide a second depth of field image with a second depth of field, where the third camera is arranged in the aperture in the first optical system; and
   where a ratio between the second depth of field and the first depth of field is in the range of 10 to 2000, and a region of the aperture, where the light rays are selected from, is less than 30% of an area of the aperture.

2. The scanner according to claim 1, wherein the second camera is adapted for forming at least one image in 1D and/or 2D of at least some of the selected light rays.

3. The scanner according to claim 1, wherein the second depth of field image has the same perspective as the first depth of field image.

4. The scanner according to claim 1, wherein the focusing optics is arranged outside the path of the selected portion of the returned light rays to the second camera such that the second depth of field image is unaffected by varying the position of the focus plane on the object.

5. The scanner according to claim 1, wherein the optics for selecting a portion of light rays is arranged in front of the focusing optics such that the selected light rays are transmitted to the second camera without intersecting the focusing optics when returning from the object.

6. The scanner according to claim 1, wherein the selected portion of light rays are directed to a second optical system for imaging onto the second camera, where the second optical system at least partly determines the second depth of field.

7. The scanner according to claim 1, wherein the first camera and the second camera are adapted to operate simultaneously.

8. The scanner according to claim 1, wherein the second optical element in the aperture is a mirror, a beam splitter, or a filter adapted to select light rays of one or more specific wavelengths.

9. The scanner according to claim 1, wherein the probe light is white light.

10. The scanner according to claim 1, wherein the scanner comprises a second light source for generating a probe light which is not used for determining the in-focus positions.

11. The scanner according to claim 10, wherein the second light source generates white light.

12. The scanner according to claim 10, wherein the second light source is LEDs of different colors.

13. The scanner according to claim 2, wherein the points in the 1D image are spectrally analyzed.

14. The scanner according to claim 13, wherein the 1D spectral analysis is performed on the second camera comprising a 2D array, where one axis of the camera array corresponds to a spatial coordinate on the object being scanned and the other axis of the camera array corresponds to a wavelength coordinate of the light returned from the object.

15. The scanner according to claim 13, wherein the spectral analysis is performed by means of a diffractive optical component.

16. The scanner according to claim 15, wherein the diffractive optical component comprises a grating, a prism or a color gradient film.

17. The scanner according to claim 1, wherein the scanner is an intra-oral scanner for scanning of at least part of a patient's set of teeth, a scan of at least part of an impression of the patient's set of teeth, and/or a scan of at least part of a model of the patient's set of teeth.

18. A scanner for obtaining and/or measuring a 3D geometry of at least a part of a surface of an object, said scanner comprising:
 a first camera comprising an array of sensor elements,
 a first means for generating probe light rays,
 means for transmitting the probe light rays towards the object thereby illuminating at least a part of the object,
 means for transmitting light rays returned from the object to the array of sensor elements,
 a first optical system for imaging with a first depth of field on the first camera at least part of the transmitted light rays returned from the object to the array of sensor elements,
 means for varying the position of the focus plane on the object,
 means for obtaining at least one image from said array of sensor elements,
 means for determining the in-focus position(s) of:
  each of a plurality of the sensor elements for a range of focus plane positions, or
  each of a plurality of groups of the sensor elements for a range of focus plane positions, and
 means for transforming the in-focus data into 3D coordinates;
 the scanner further comprising:
 means for selecting a portion of light rays returned from the object, where the light rays have been transmitted through at least a part of the first optical system, and where the means for selecting a portion of light rays returned from the object includes an optical element that is arranged in an aperture in the first optical system; and a second camera for capturing at least some of the selected light rays to provide a second depth of field, or
 a third camera arranged to capture a portion of the light rays returned from the object, where the light rays have been transmitted through at least a part of the first optical system, to provide a second depth of field image with a second depth of field, where the third camera is arranged in the aperture in the first optical system; and
 where a ratio between the second depth of field and the first depth of field is in the range of 10 to 2000, and a region of the aperture, where the light rays are selected from, is less than 30% of an area of the aperture.

19. The scanner according to claim 18, wherein the scanner comprises the third camera arranged to capture at least some of the selected light rays to provide a second depth of field image with a second depth of field, where the third camera is arranged in the aperture in the first optical system.

20. The scanner according to claim 18, wherein the scanner comprises the means for selecting a portion of the light rays returned from the object, where the light rays have been transmitted through at least a part of the first optical system, and where the means for selecting a portion of light rays returned from the object includes a second optical element that is arranged in an aperture in the first optical system; and the second camera is arranged to capture at least some of the selected light rays to provide a second depth of field image with a second depth of field.

21. The scanner according to claim 1, wherein the scanner comprises the optics for selecting a portion of the light rays returned from the object, where the light rays have been transmitted through at least a part of the first optical system, and where the optics for selecting a portion of light rays returned from the object includes a second optical element that is arranged in an aperture in the first optical system; and the second camera is arranged to capture at least some of the selected light rays to provide a second depth of field image with a second depth of field.

22. The scanner according to claim 1, wherein the scanner comprises the third camera arranged to capture at least some of the selected light rays to provide a second depth of field image with a second depth of field, where the third camera is arranged in the aperture in the first optical system.

* * * * *